US012748108B2

(12) United States Patent
Jung et al.

(10) Patent No.: US 12,748,108 B2
(45) **Date of Patent: *Sep. 29, 2026**

(54) POCT DIAGNOSTIC SYSTEM FOR TRAUMATIC BRAIN INJURIES AND INFECTIOUS DISEASES

(71) Applicant: EZDIATECH INC., Cheonan-si (KR)

(72) Inventors: Yong Gyun Jung, Seoul (KR); Joo Ho Kim, Yongin-si (KR)

(73) Assignee: EZDIATECH INC., Cheonan-si (KR)

( * ) Notice: Subject to any disclaimer, the term of this patent is extended or adjusted under 35 U.S.C. 154(b) by 1201 days.

This patent is subject to a terminal disclaimer.

(21) Appl. No.: 17/777,593

(22) PCT Filed: Sep. 25, 2020

(86) PCT No.: PCT/KR2020/013024
§ 371 (c)(1),
(2) Date: May 17, 2022

(87) PCT Pub. No.: WO2021/060897
PCT Pub. Date: Apr. 1, 2021

(65) Prior Publication Data

US 2023/0341382 A1 Oct. 26, 2023

(30) Foreign Application Priority Data

Sep. 27, 2019 (KR) ........................ 10-2019-0119565

(51) Int. Cl.
*G01N 33/543* (2006.01)
*G01N 33/575* (2026.01)
*G01N 35/00* (2006.01)

(52) U.S. Cl.
CPC . *G01N 33/54333* (2013.01); *G01N 33/54353* (2013.01); *G01N 33/575* (2026.01);
(Continued)

(58) Field of Classification Search
CPC ........... G01N 33/54333; G01N 33/574; G01N 33/54326; G01N 33/5434;
(Continued)

(56) References Cited

U.S. PATENT DOCUMENTS 9,745,438 B2 8/2017 Bedre et al.
12,493,028 B2 * 12/2025 Jung ................ G01N 33/54326
(Continued)

FOREIGN PATENT DOCUMENTS

JP 6080164 B2 2/2017
KR 100821192 B1 4/2008
(Continued)

OTHER PUBLICATIONS

International search report of PCT/KR2020/013024, Jan. 7, 2021, English translation.
(Continued)

*Primary Examiner* — Gailene Gabel
(74) *Attorney, Agent, or Firm* — STIP Law Group, LLC

(57) ABSTRACT

The present invention relates to a POCT diagnostic system that can quickly identify traumatic brain injuries and infectious diseases and can accurately determine traumatic brain injuries and infectious diseases with high sensitivity. The present invention provides magnetic particles including a core including a magnetically responsive metal, a shell layer surrounding the core and having a uniform thickness, and capture probes introduced onto the shell layer to capture biological materials. Each of the capture probes includes an antibody against a biomarker for the diagnosis of a traumatic brain injury or infectious disease as an antigen.

15 Claims, 17 Drawing Sheets

(52) U.S. Cl.
CPC .................. *G01N 33/57557* (2026.01); *G01N 2035/00564* (2013.01); *G01N 2800/7028* (2013.01)

(58) Field of Classification Search
CPC ........... G01N 33/54353; G01N 33/575; G01N 33/57557; G01N 35/0098; G01N 2800/00
See application file for complete search history.

(56) References Cited

U.S. PATENT DOCUMENTS

| | | | | |
|---|---|---|---|---|
| 2004/0026684 | A1* | 2/2004 | Empedocles ........ | H10D 62/125 257/14 |
| 2005/0255514 | A1* | 11/2005 | De Palma .............. | B82Y 40/00 435/6.12 |
| 2013/0029362 | A1 | 1/2013 | Jeromin et al. | |
| 2013/0195963 | A1* | 8/2013 | Serda ...................... | A61K 40/24 424/490 |
| 2020/0246866 | A1* | 8/2020 | Park ........................ | D21H 21/42 |
| 2021/0341470 | A1* | 11/2021 | Jung ..................... | G01N 33/581 |
| 2023/0341383 | A1* | 10/2023 | Jung ................ | G01N 33/54333 |

FOREIGN PATENT DOCUMENTS

| | | | |
|---|---|---|---|
| KR | 20110008400 | A | 1/2011 |
| KR | 20140094035 | A | 7/2014 |
| KR | 20140098285 | A | 8/2014 |
| KR | 101845552 | B1 | 4/2018 |
| KR | 20180079150 | A | 7/2018 |
| KR | 20180118670 | A | 10/2018 |
| KR | 20180130436 | A | 12/2018 |

OTHER PUBLICATIONS

O.Y. Galkin et al, Modern magnetic immunoassay: Biophysical and biochemical aspects, Regulatory Mechanisms in Biosystems, Nov. 19, 2017, pp. 47-55, vol. 9, Issue 1, Dnipro, Ukraine.

* cited by examiner

[Fig. 1]
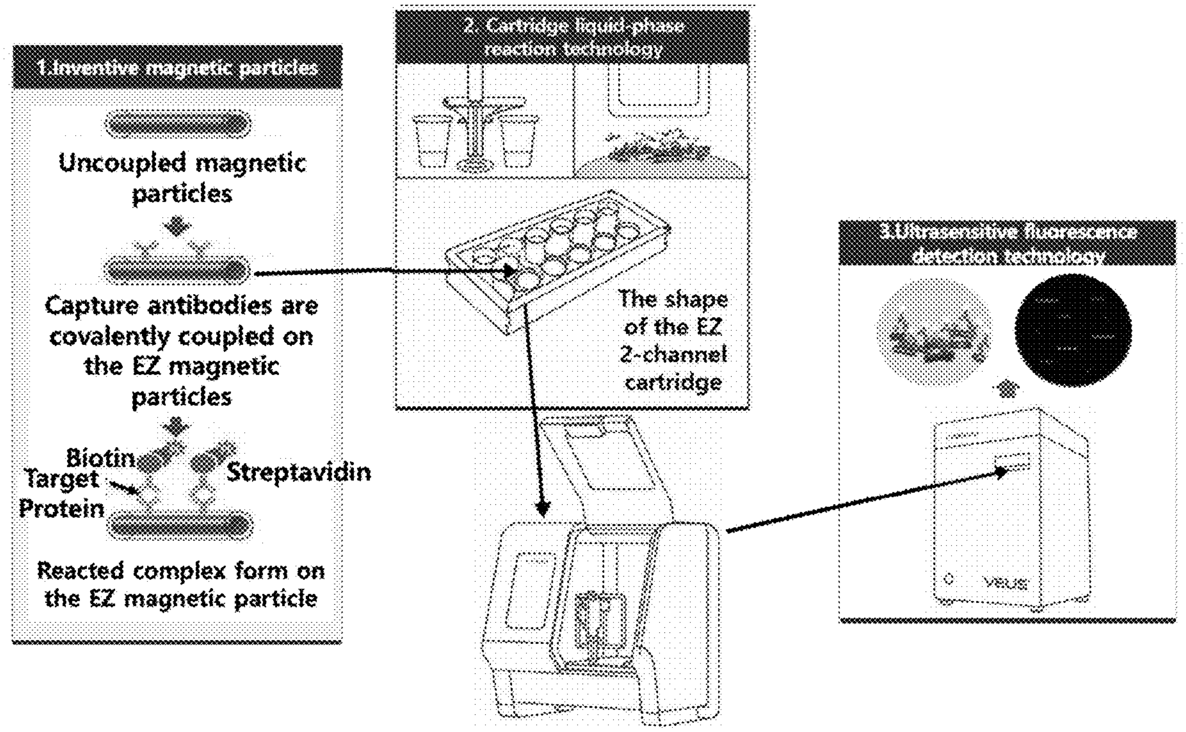

[Fig. 2]
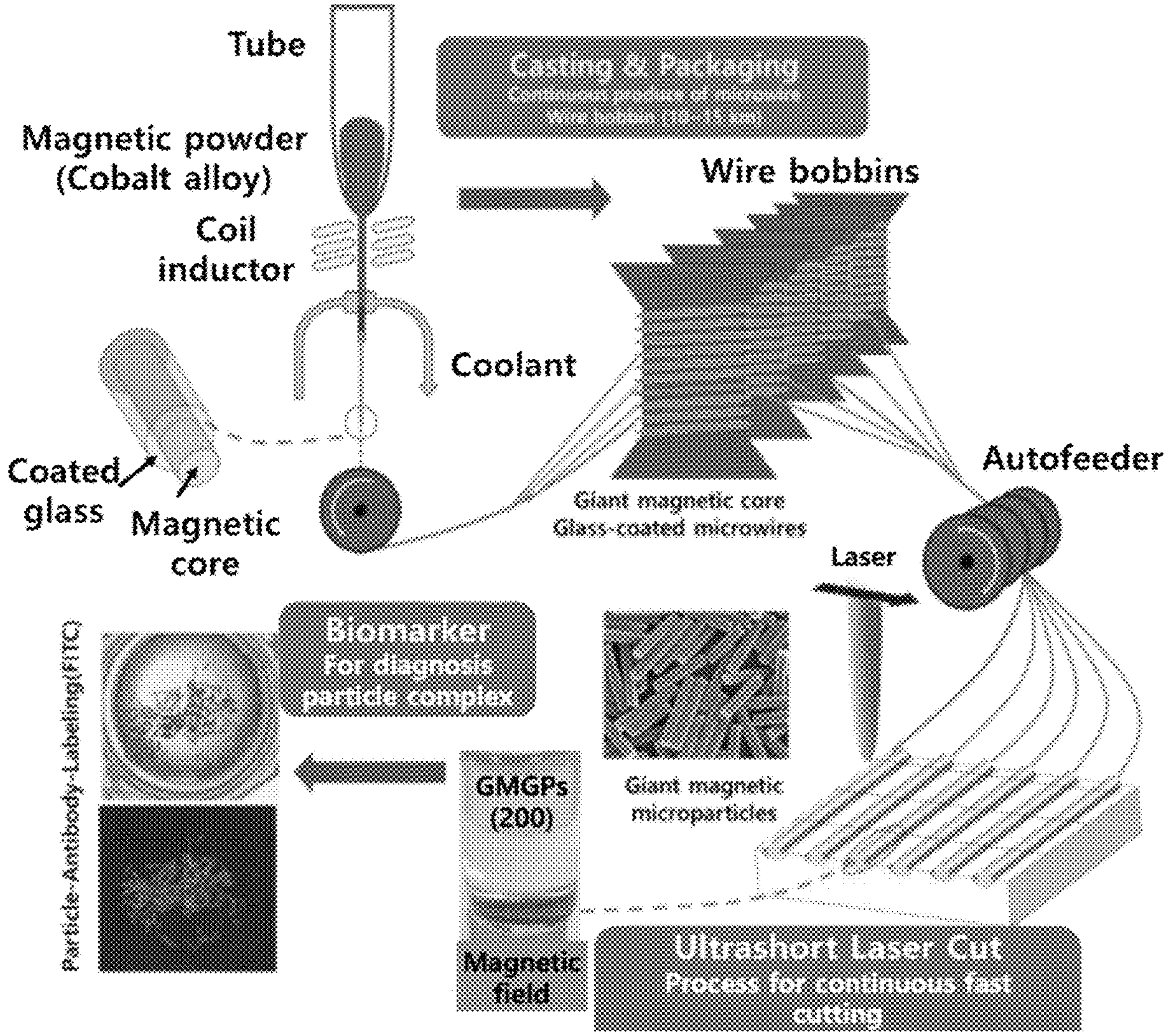

[Fig. 3]
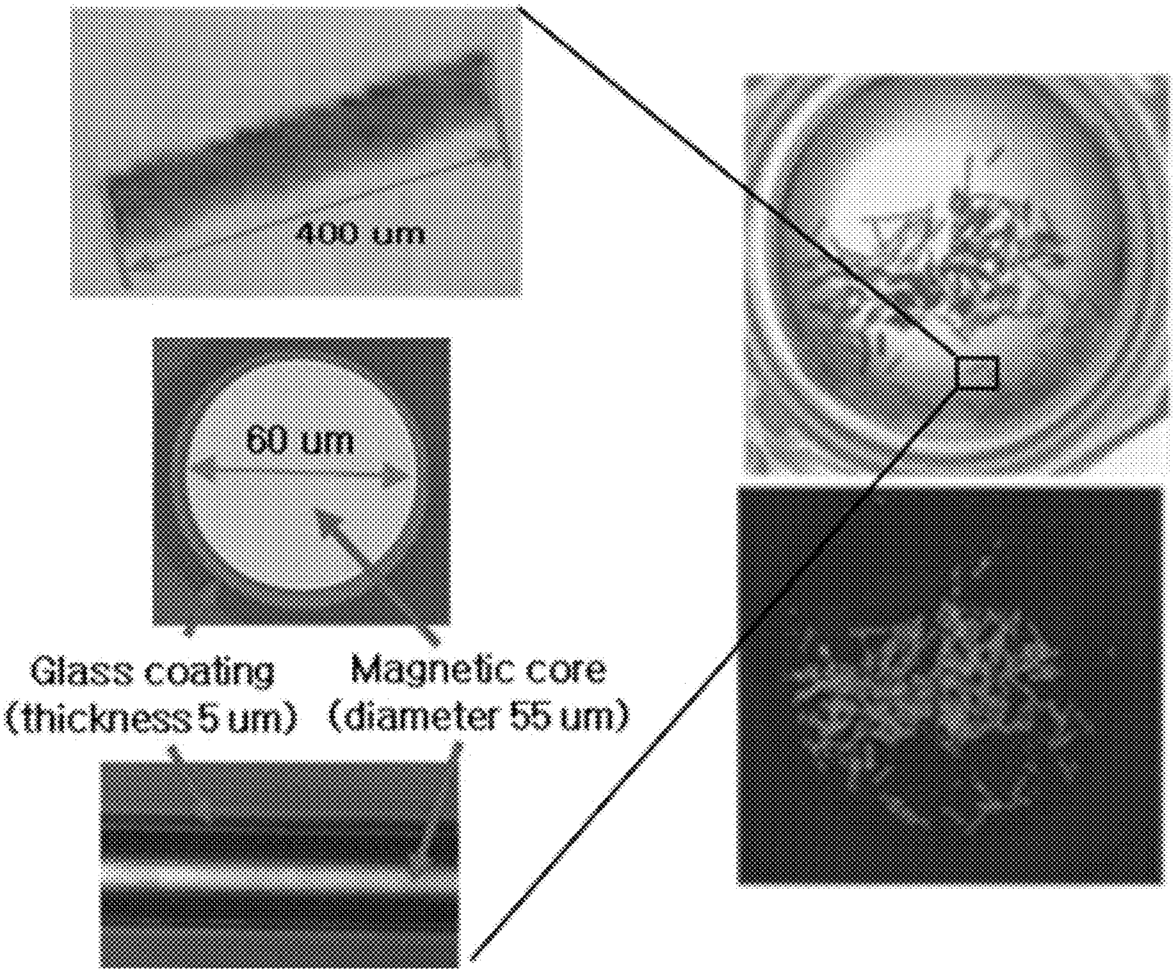

[Fig. 4]
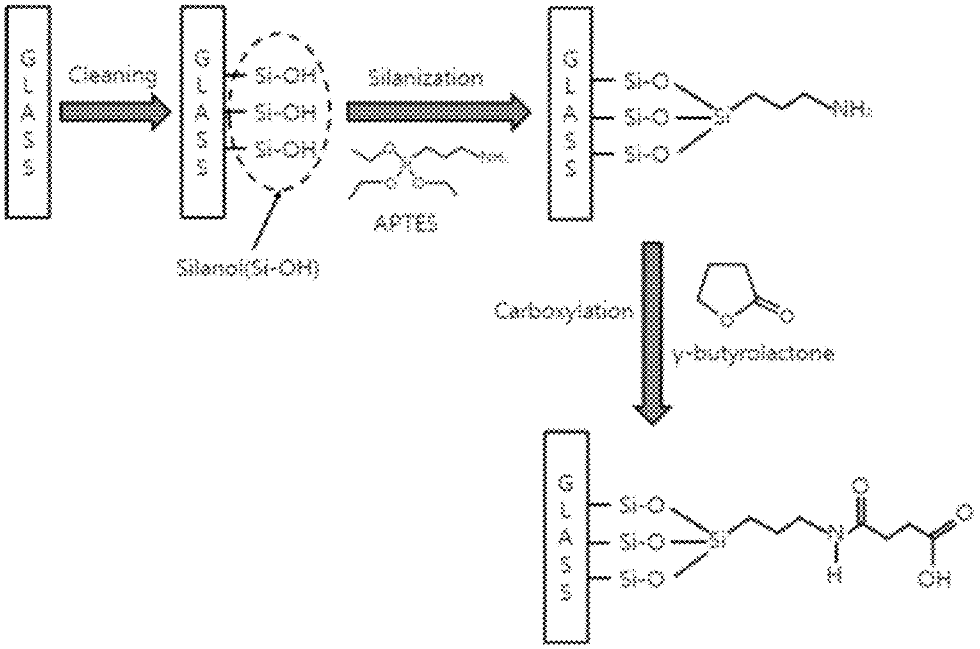
[Fig. 5 (a)]
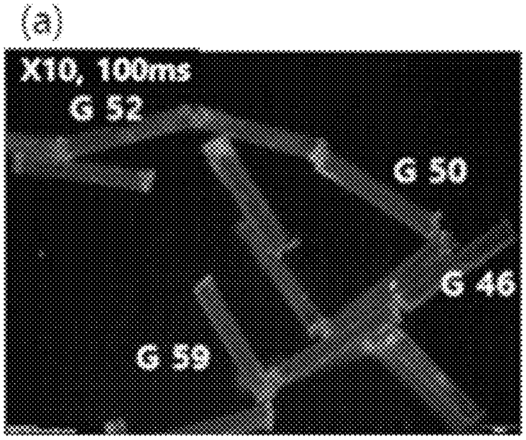
[FIG. 5(b)]
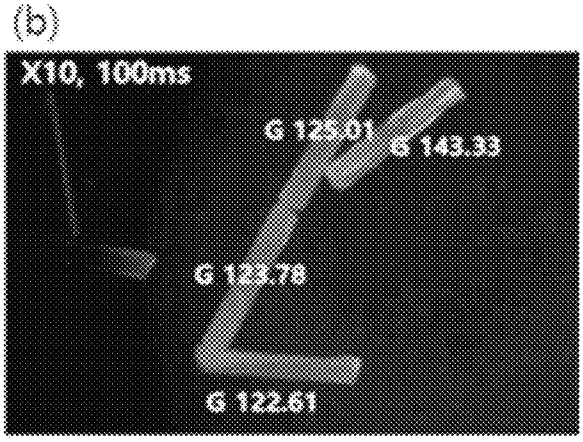

[Fig. 6(a)]
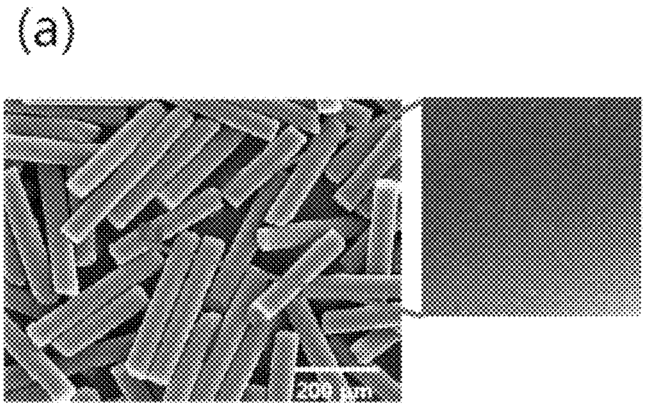
[Fig. 6(b)]
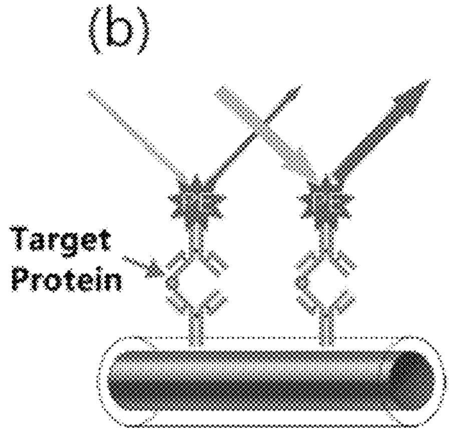
[FIG. 6(c)]
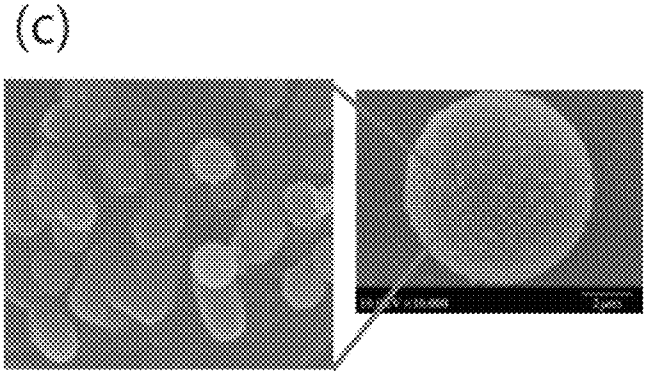
[FIG. 6(d)]
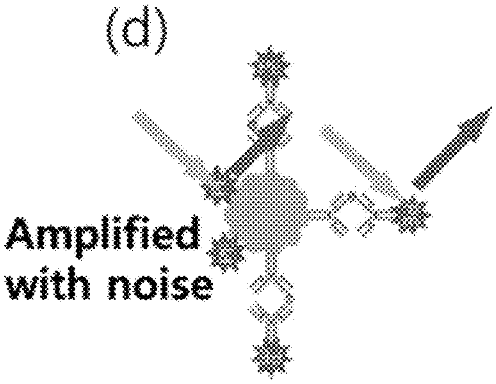

[Fig. 7(a)]
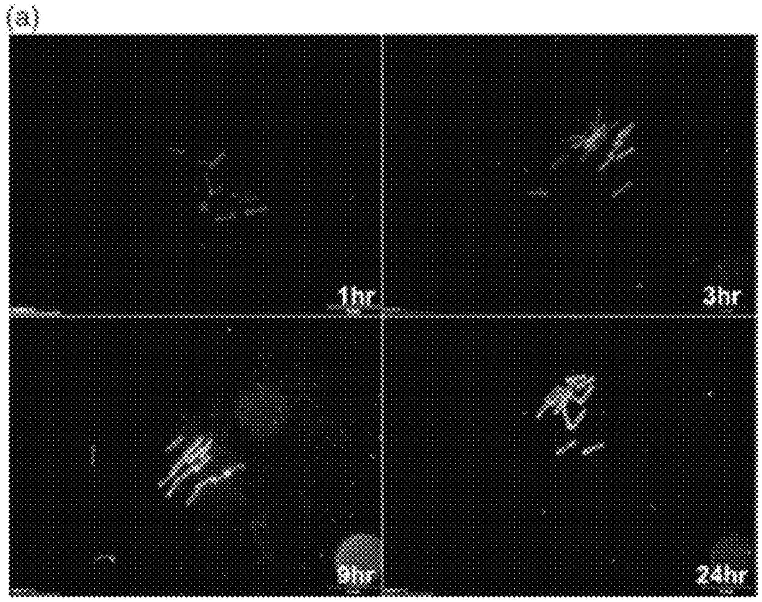
[Fig. 7(b)]
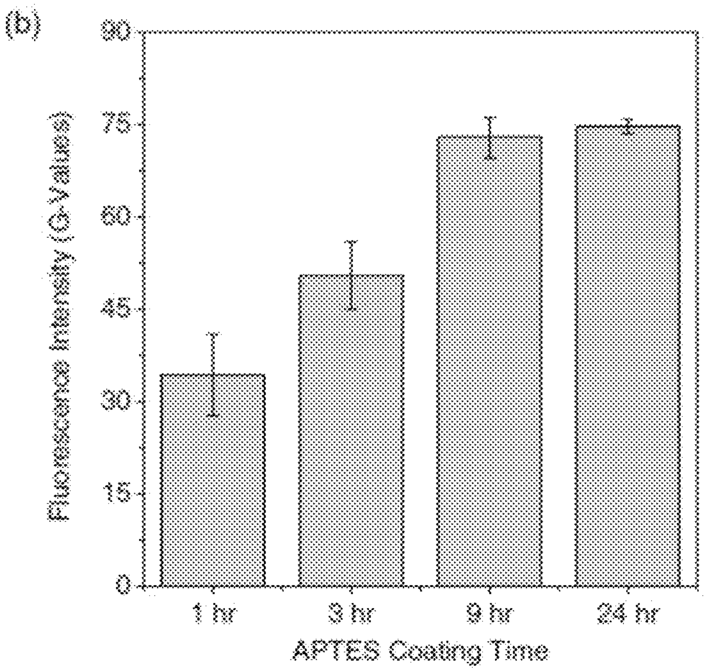

[Fig. 8]
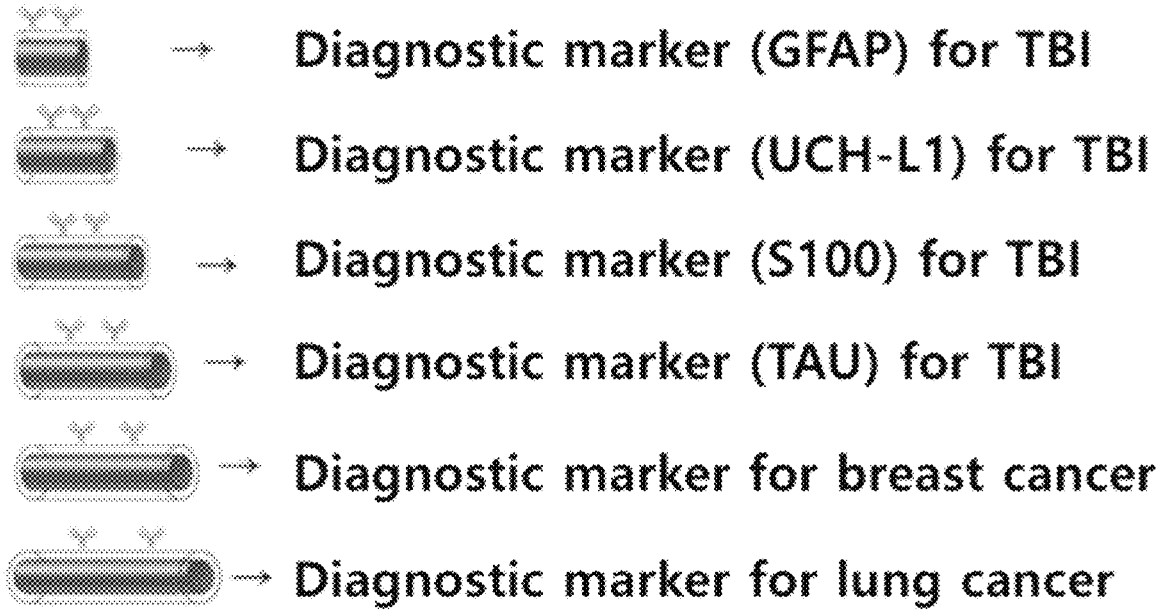

[Fig. 9]
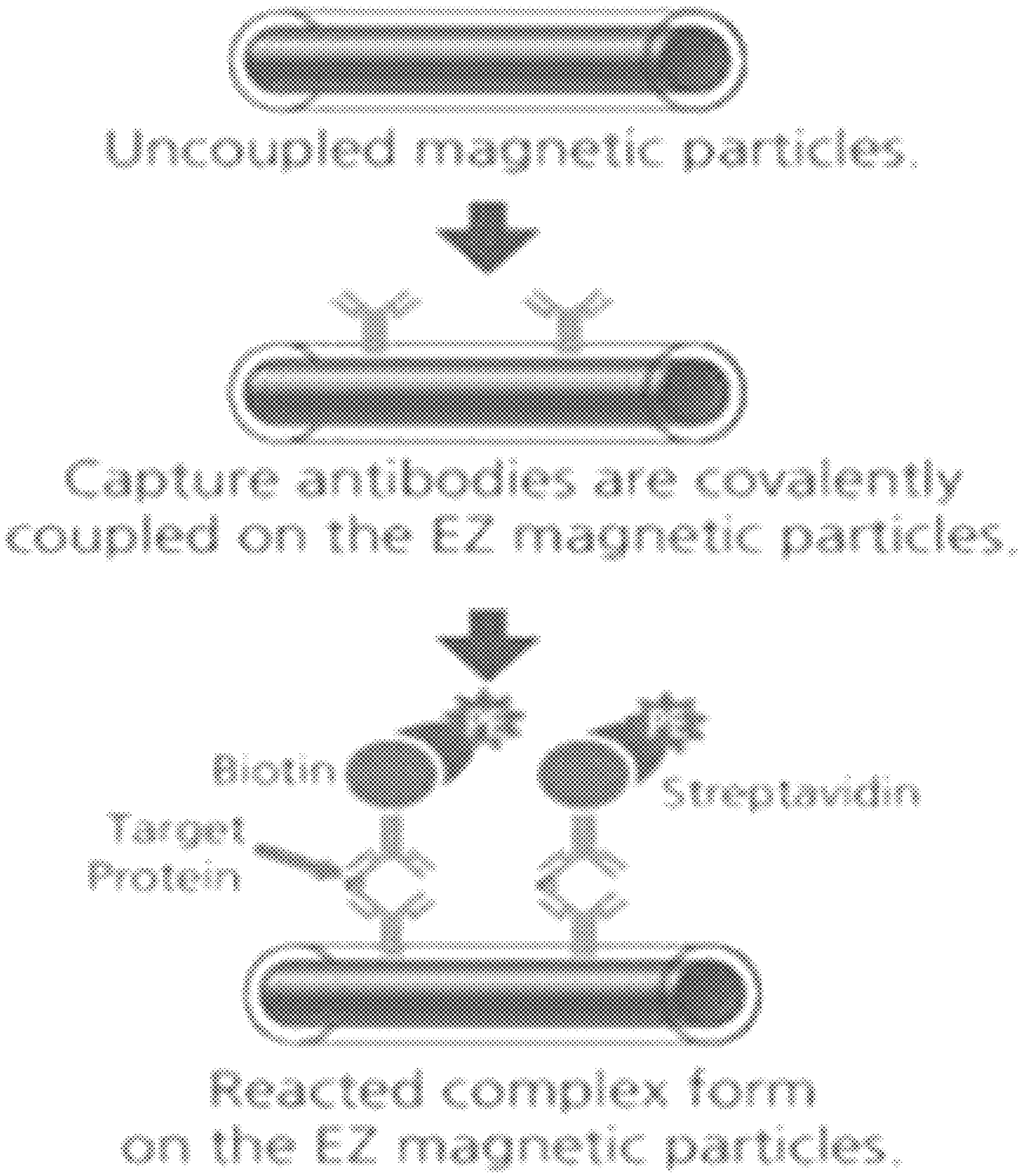

[Fig. 10]
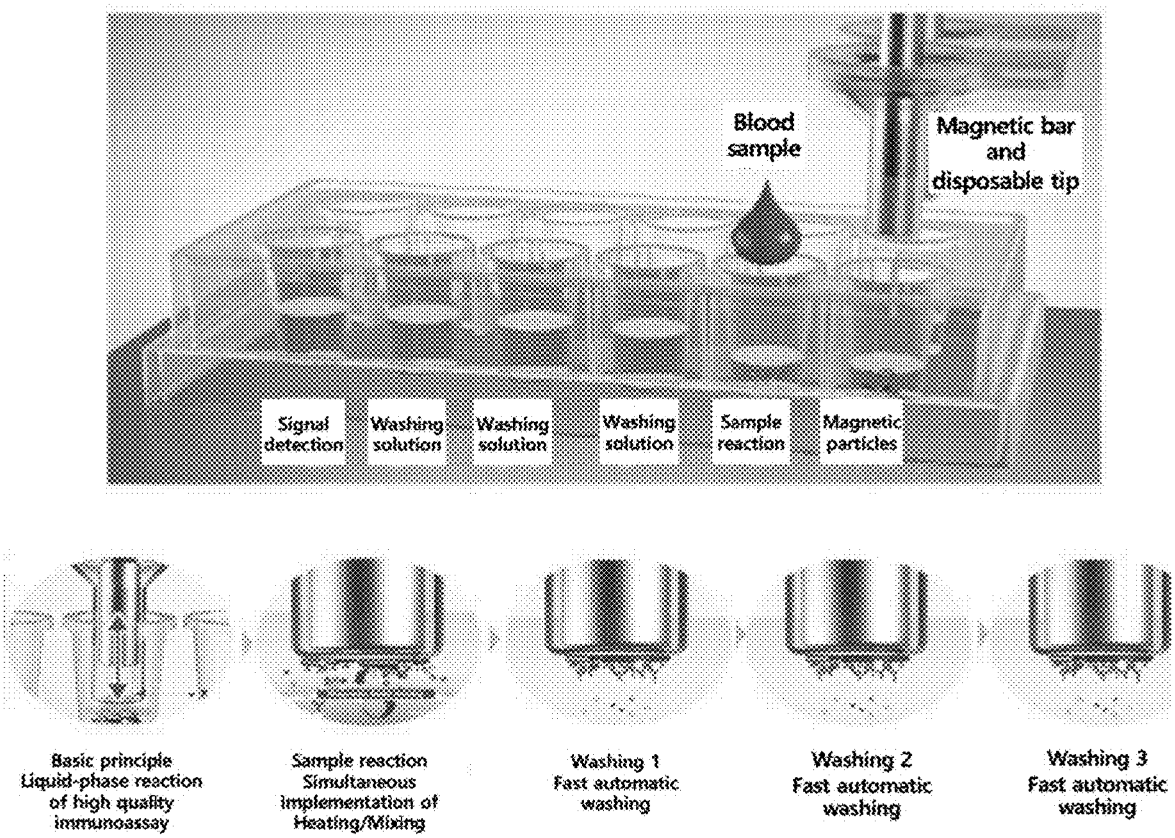

[Fig. 11(a)]
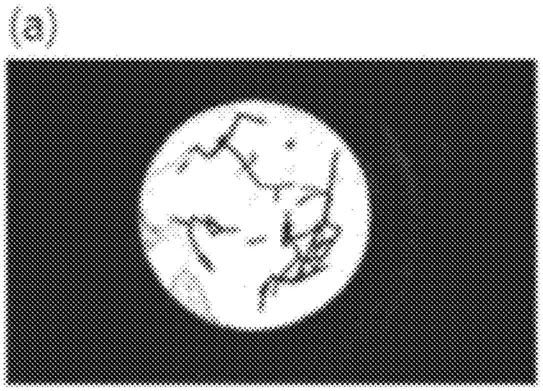
[Fig. 11(b)]
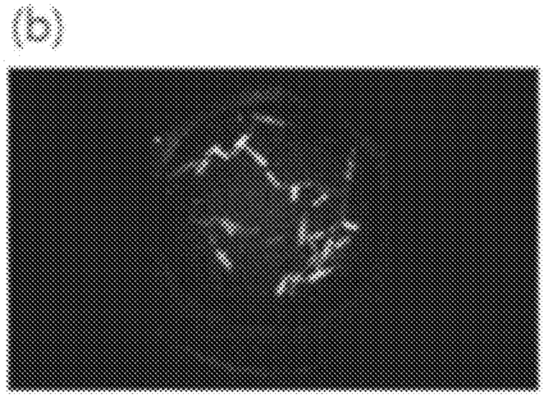
[Fig. 11(c)]
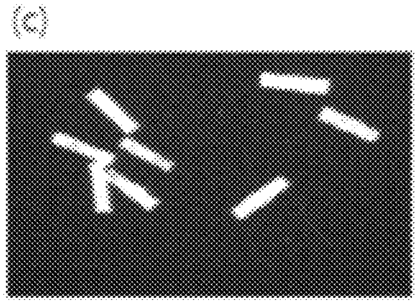
[Fig. 11(d)]
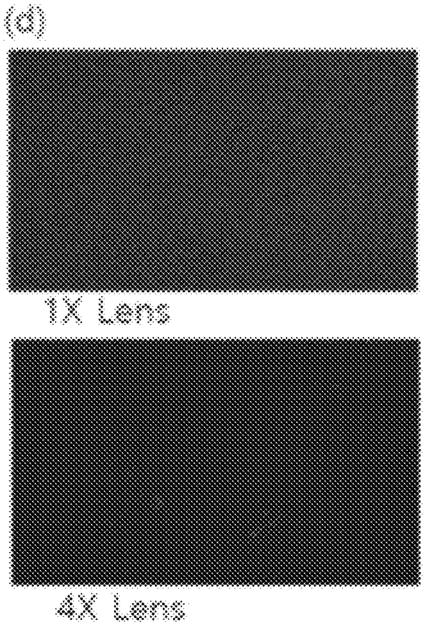

[Fig. 12]
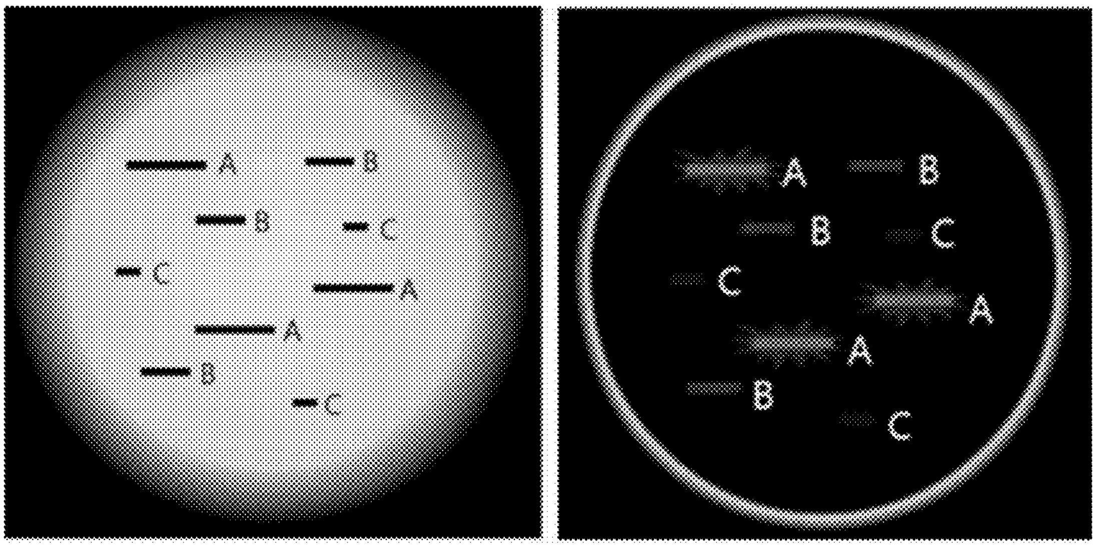
[Fig. 13]
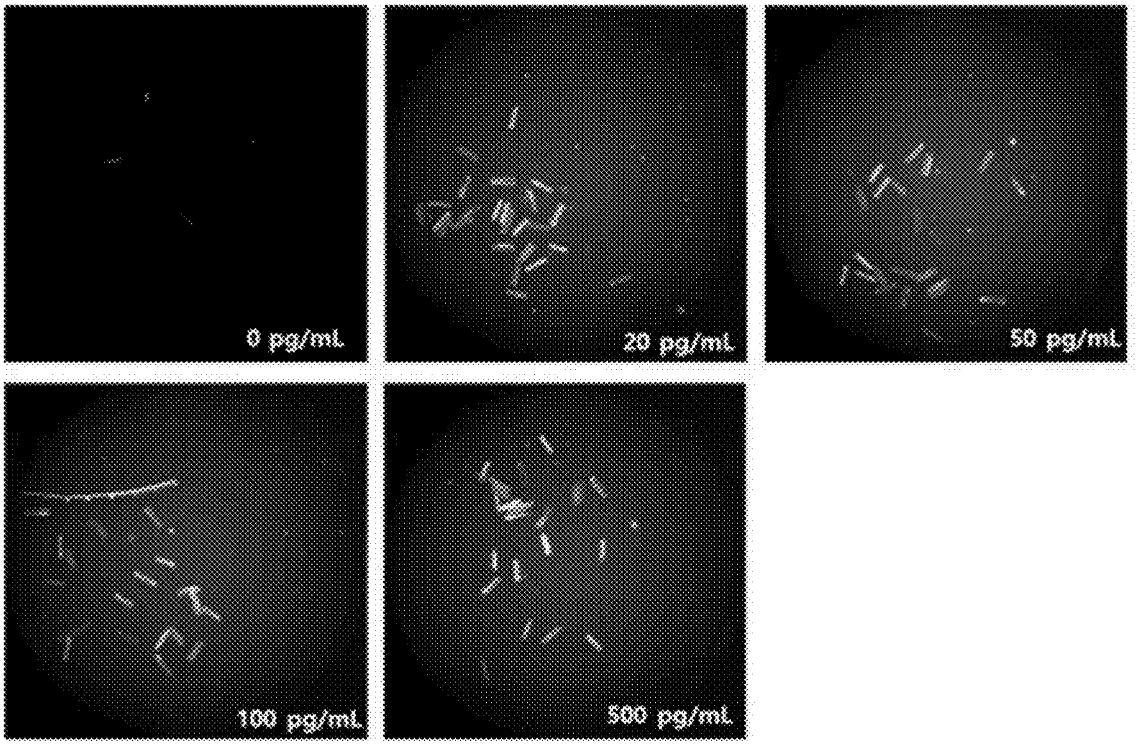

[Fig. 14]
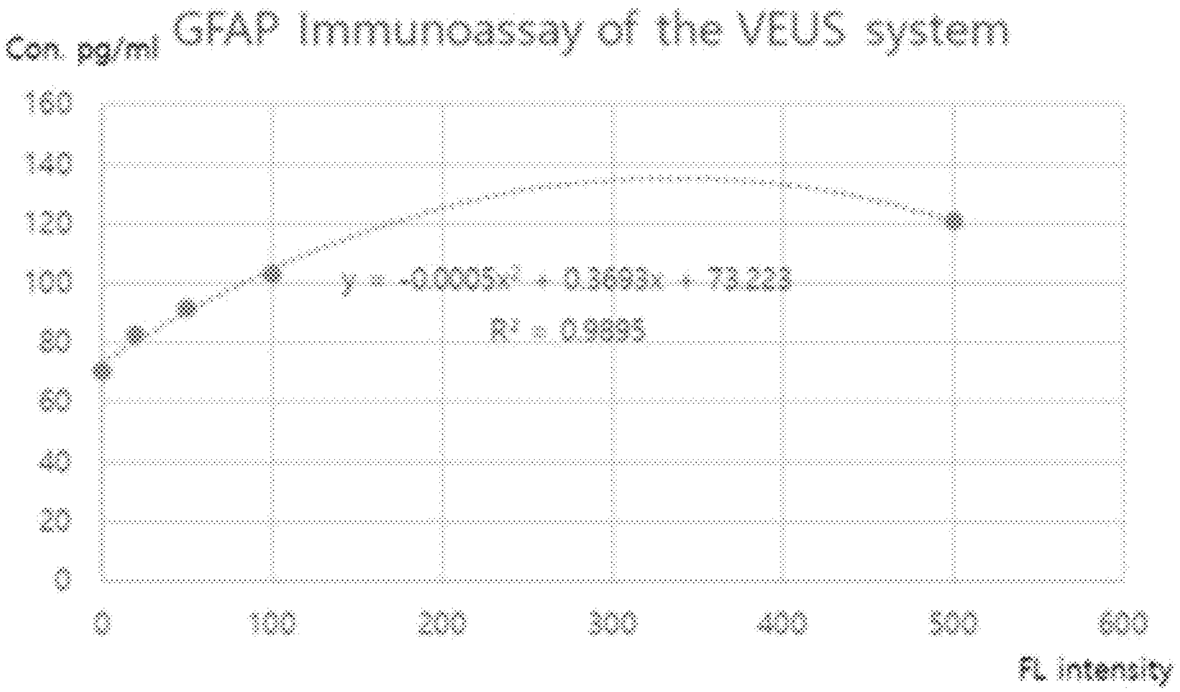

[Fig. 15]
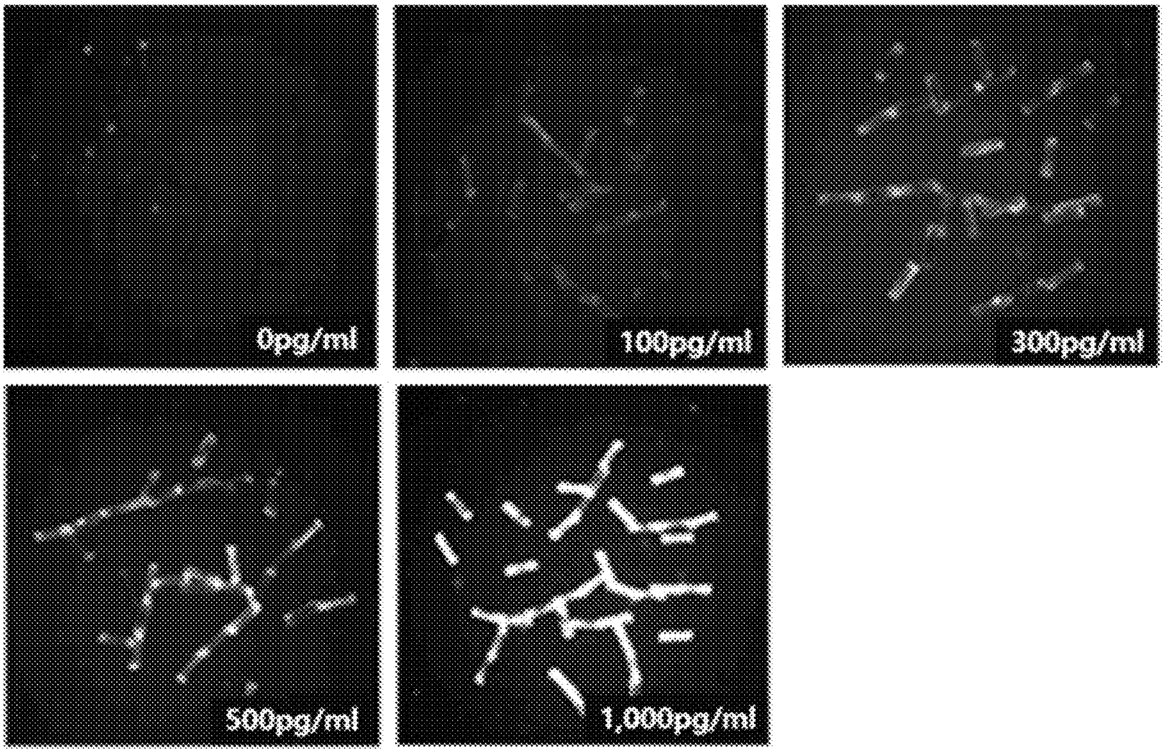
[Fig. 16]
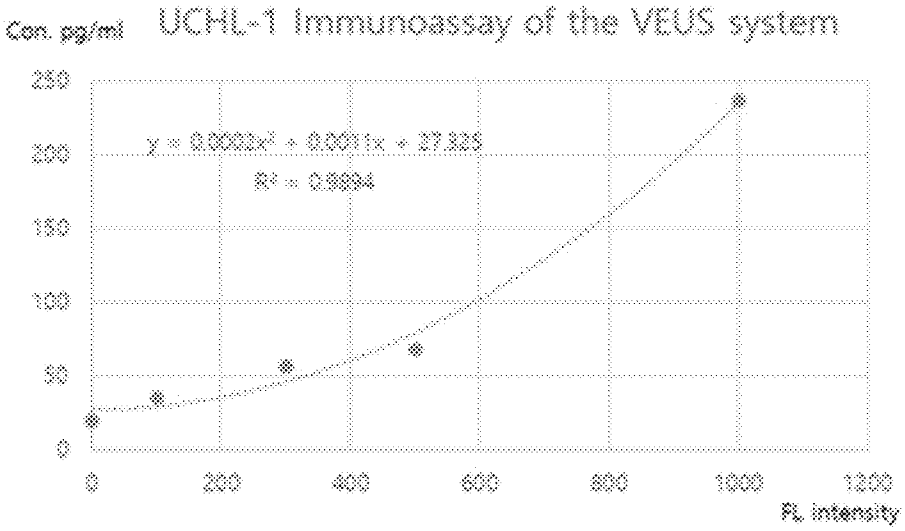

[Fig. 17(a)]
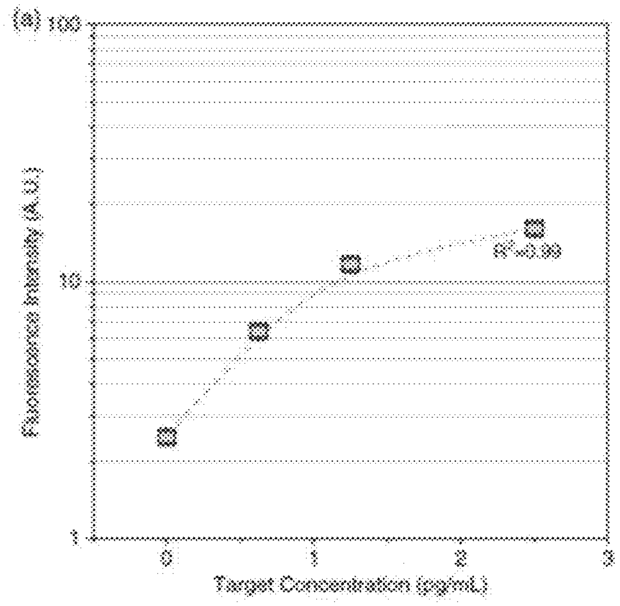
[Fig. 17(b)]
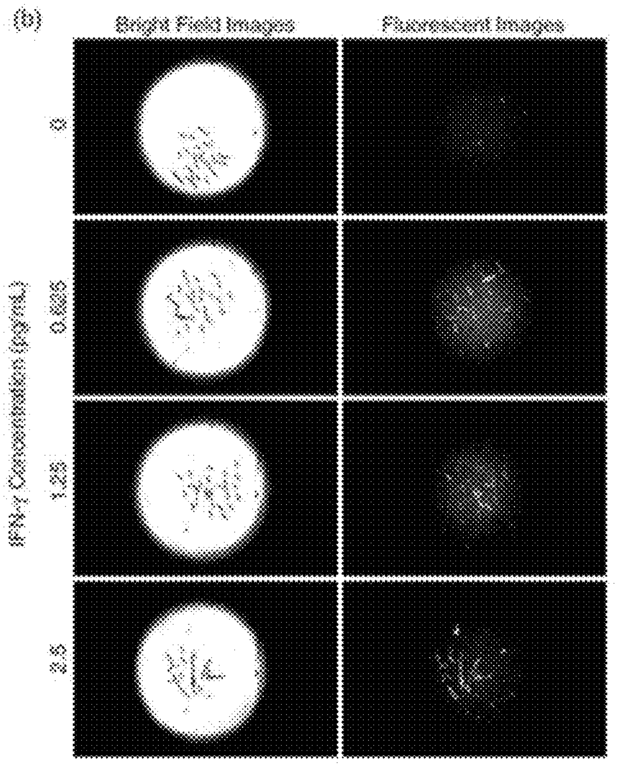

[Fig. 18(a)]
(a)
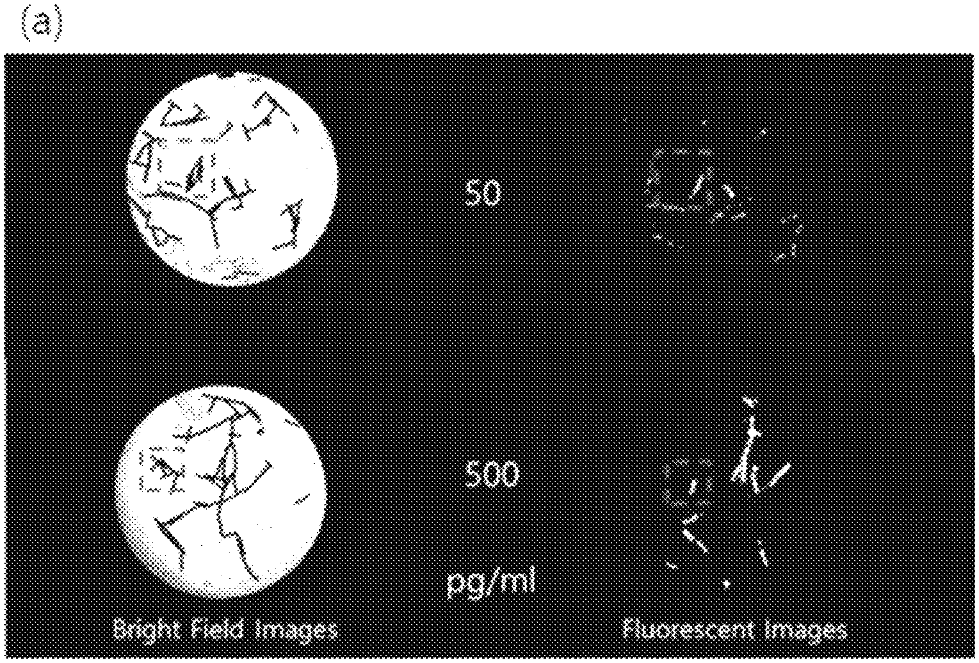
[Fig. 18(b)]
(b)
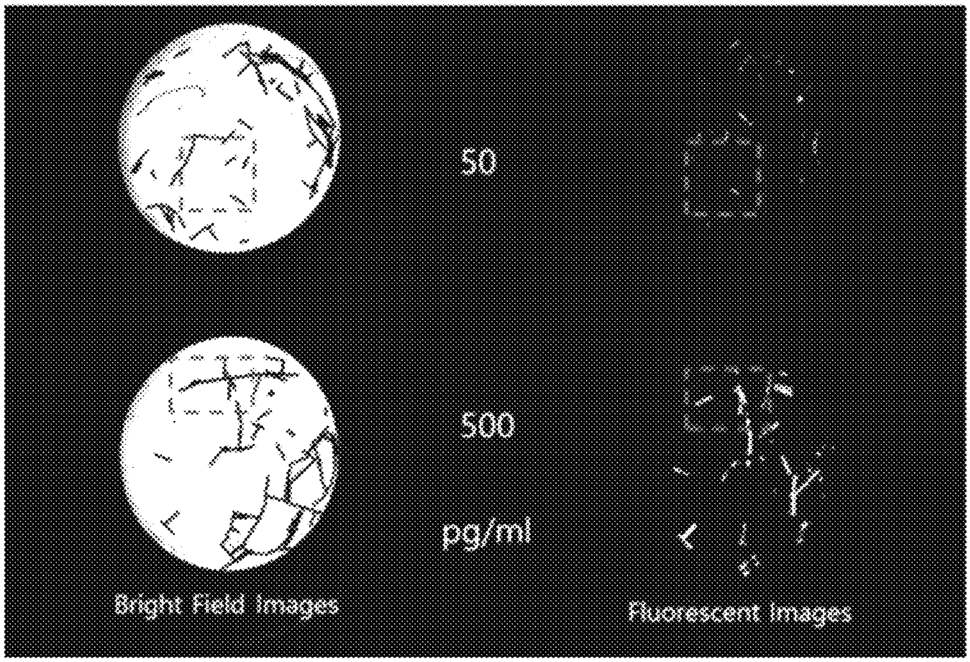

[Fig. 19]
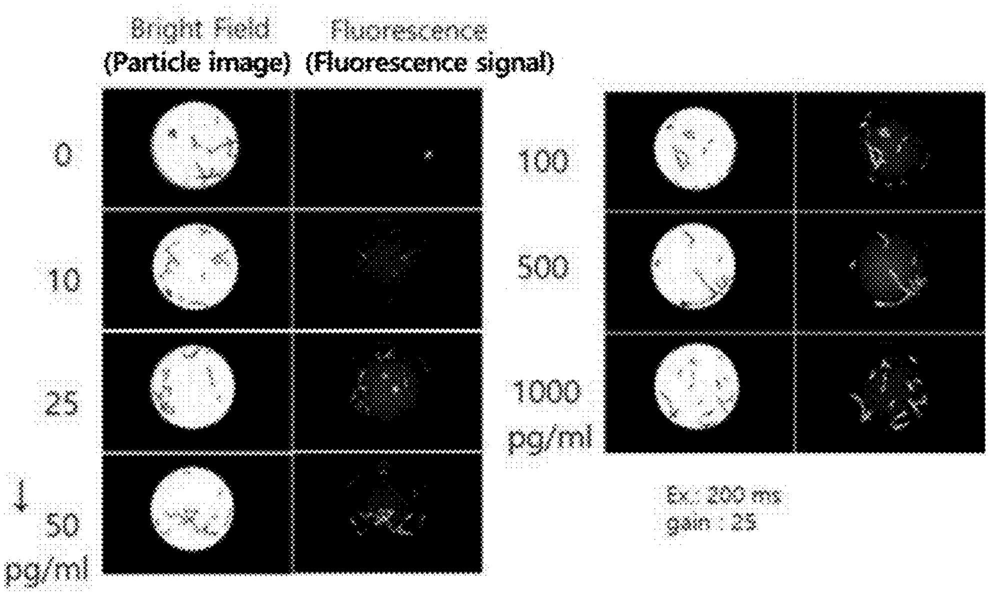
[Fig. 20]
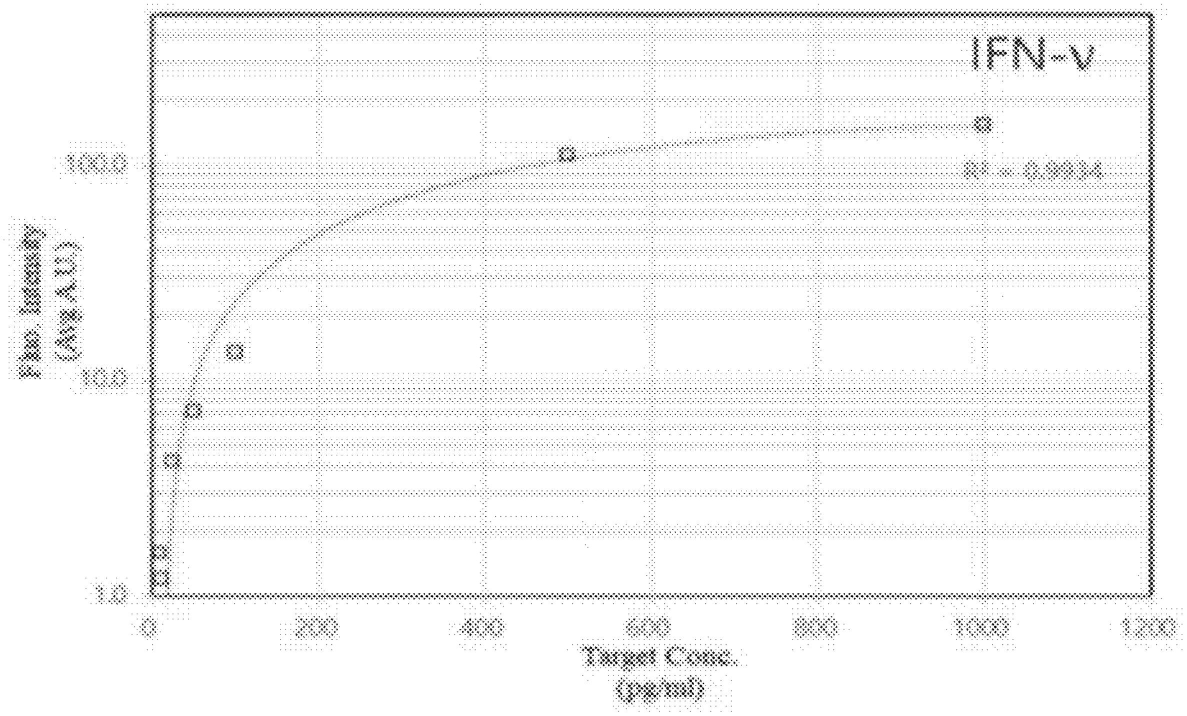

[Fig. 21]
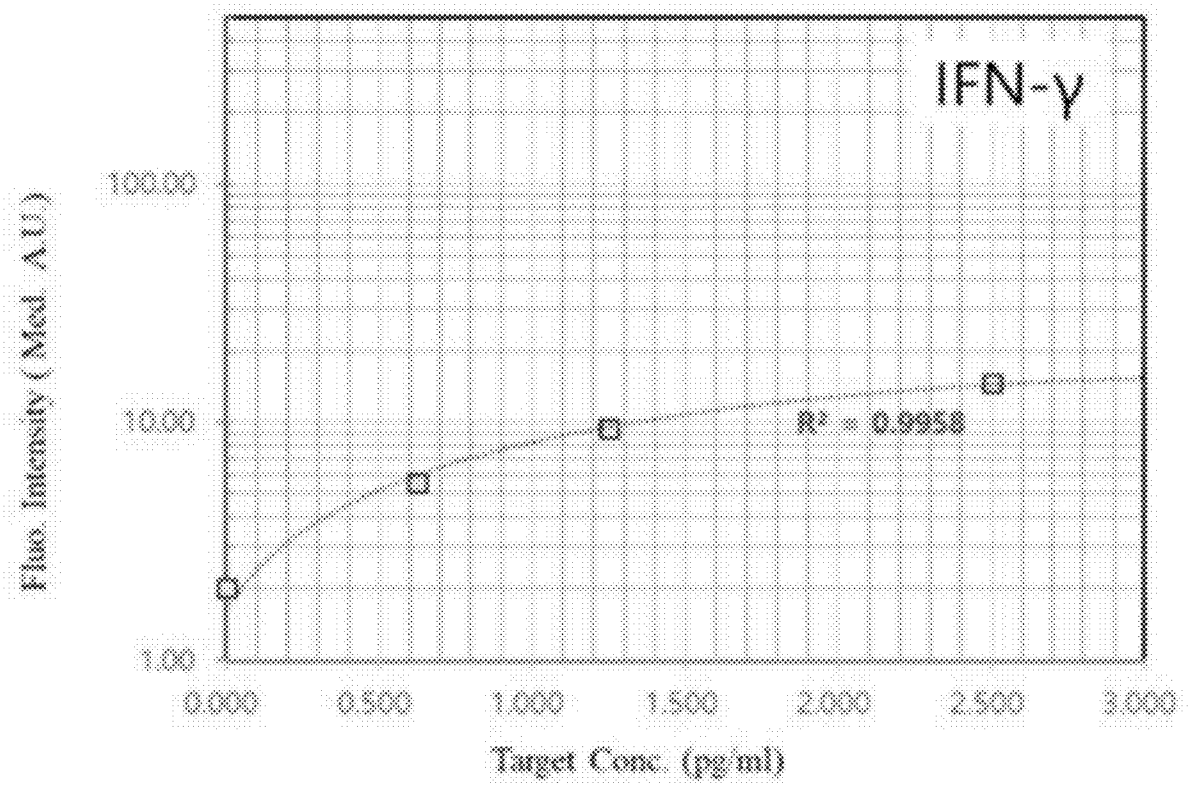

POCT DIAGNOSTIC SYSTEM FOR TRAUMATIC BRAIN INJURIES AND INFECTIOUS DISEASES

CROSS-REFERENCE TO RELATED APPLICATIONS

This application is the U.S. National Phase under 35 U.S.C. § 371 of International Application No. PCT/KR2020/013024 filed on Sep. 25, 2020, which in turn claims the benefit of Korean Application No. 10-2019-0119565 filed on Sep. 27, 2019, the disclosures of which are incorporated by reference into the present application.

TECHNICAL FIELD

The present invention relates to a novel POCT diagnostic system for traumatic brain injuries and infectious diseases, and more specifically to a POCT diagnostic system that can quickly identify traumatic brain injuries and infectious diseases and can accurately determine traumatic brain injuries and infectious diseases with high sensitivity.

BACKGROUND ART

In vitro diagnostics (IVD) is a technique for analyzing samples (e.g., blood, urine, and cells) collected from humans to diagnose human health. Such in vitro diagnostic methods include immunodiagnostics, self-blood glucose monitoring, and molecular diagnostics. Particularly, immunodiagnostic techniques can be used to diagnose and track a wide variety of diseases by determining the presence or absence of specific pathogenic proteins based on antigen-antibody reactions. However, the presence of target proteins at concentrations above the limits of detection is a prerequisite for the utilization of immunodiagnostic techniques. Due to this disadvantage, various techniques have been developed to amplify signals generated from low concentrations of proteins.

Particularly, with recent advances in synthetic chemistry and bioscience, various target analytes have appeared in a variety of fields, including new drug development and diagnostics. Several highly sensitive methods have been reported to detect minute amounts of targets using magnetic particles that ensure the generation of signals (Modern magnetic immunoassay: Biophysical and biochemical aspects (2017) Regul. Mech. Biosyst., 9(1), 47-55).

Conventional immunodiagnostic techniques use nanometer-sized magnetic particles surface modified with silica. However, such silica-modified magnetic particles are not effectively extracted or released from wells where immune reactions occur. That is, small-sized magnetic particles are often present in a suspended form in solutions and are thus difficult to separate. For this reason, small-sized magnetic particles are used for qualitative analysis rather than quantitative analysis. Further, conventional analytical methods require a long testing time and involve a complex test procedure because they can test only one magnetic particle at a time.

Traumatic brain injury (TBI) refers to damage to the brain tissue caused by an external impact. Traumatic brain injury can be classified into "mild", "moderate", and "severe" by their severity after determining Glasgow coma scale (GCS), post-traumatic amnesia (PTA), and loss of consciousness (LOC). Particularly, mild TBI (mTBI) accounts for the largest proportion of all TBIs. The reality is that most patients suspected of mTBI visit small and medium-sized hospitals. CT and MRI are presented as sole diagnostic tools for mTBI but are difficult to use for diagnostic applications in small and medium-sized hospitals because they are expensive and need professional operation skills. Moreover, CT and MRI provide highly false negative results because they can detect only 10% or less of mTBI patients and fail to provide accurate results for patients. CT and MRI require a long time for diagnosis, incur high costs, and have a disadvantage in that patients bear the risk of exposure to radiation.

Thus, there is a need for a new TBI diagnostic system that is more accurate and safer. mTBI diagnosis should be fast and accurate with a test time of less than 1 hour for its application to emergency situations, should be able to obtain results from small amounts of samples, and requires testing of two or more biomarkers at one time with high sensitivity. In addition, mTBI diagnosis requires a simple test with a small-sized system and a low maintenance and management cost for its application to emergency rooms and small and medium-sized hospitals.

Banyan Biomarker, U.S. launched the world's first blood diagnostic product ("Banyan BTI™") based on enzyme-linked immunosorbent assay (ELISA). Although Banyan BTI™ is known to provide more accurate results than conventional blood diagnostic products, it requires a long test time (3-4 hours) and needs trained manpower and expensive equipment, making it impossible to use in small- and medium-sized hospitals, like CT or MRI, and being unsuitable for multiplexed detection.

DETAILED DESCRIPTION OF THE INVENTION

Problems to be Solved by the Invention

The present invention has been made in an effort to solve the above-described problems and intends to provide magnetic particles for diagnosing a traumatic brain injury that can quickly identify traumatic brain injuries and can accurately determine traumatic brain injuries with high sensitivity, a method for preparing the magnetic particles, and a POCT diagnostic system for traumatic brain injuries including the magnetic particles.

Means for Solving the Problems

One aspect of the present invention provides magnetic particles including a core including a magnetically responsive metal, a shell layer surrounding the core and having a uniform thickness, and capture probes introduced onto the shell layer to capture biological materials, wherein each of the capture probes includes an antibody against a biomarker for the diagnosis of a traumatic brain injury or infectious disease as an antigen.

In one embodiment, the magnetic particles may have a limit of detection of 1 pg/ml or less and a dynamic range of at least log 3.

In one embodiment, the magnetic particles may have two or more different lengths and may diagnose two or more types of biomarkers simultaneously.

In one embodiment, the hydrophilic functional groups may be silanol groups or carboxyl, amino, hydroxyl, thiol or aldehyde groups derived from silanol groups.

In one embodiment, the shell surface may have 1 to 80 hydrophilic functional groups per unit area ($nm^2$).

In one embodiment, the capture probes may be linked to the hydrophilic functional groups on the surface of the shell layer.

In one embodiment, the core may occupy 60% or more of the total volume of the magnetic particles.

In one embodiment, the shell layer may have an average surface roughness (Ra) of 15 nm or less.

In one embodiment, the shell layer may have a thickness of 1 to 100 μm.

In one embodiment, the magnetic particles may be obtained by cutting glass-coated metal micro wires.

In one embodiment, the magnetic particles may have a size and specific gravity such that they are not suspended in water.

In one embodiment, the magnetic particles may be in the form of micro rods.

In one embodiment, the micro rods may have a length of 10 to 1,000 μm.

In one embodiment, the micro rods may have an aspect ratio of at least 2.

In one embodiment, the biomarker may be one present in a sample solution derived from a living organism.

A further aspect of the present invention provides a method for preparing magnetic particles for detecting biological materials, including (i) preparing magnetic micro rods consisting of a shell made of glass and a core including a magnetic material, (ii) treating the surface of the magnetic micro rods with an acidic solution to form silanol groups, (iii) immersing the surface-treated magnetic micro rods in a silane-based solution to bind a silane compound to the silanol groups, (iv) converting the terminal groups of the silane molecules to terminal groups capable of binding to probes, and (v) attaching probes to the terminal groups of the silane molecules.

In one embodiment, step (iv) may be carried out by immersing the magnetic micro rods in a silane-based solution for 6 to 24 hours.

In one embodiment, the acidic solution may be a mixture of sulfuric acid and hydrogen peroxide.

Another aspect of the present invention provides a method for detecting biological materials, including (1) providing the magnetic particles to a first well, (2) transferring the magnetic particles from the first well to a second well using a magnetic force, (3) providing detection probes capable of specific binding to biological materials and conjugated with a luminescent material emitting light in response to an external stimulus to the second well and allowing the capture probes, the biological materials, and the detection probes to react with one another to form complexes of the magnetic particles, the biological materials, and the detection probes, and (4) transferring the magnetic particle-biological material-detection probe complexes to a third well using a magnetic force and measuring luminescence signals generated from the luminescent material present in the complexes in response to the external stimulus to detect the biological materials.

In one embodiment, the formation of the complexes may include promoting the reactions in the presence of an external magnetic force.

In one embodiment, the method may be intended for multiplexed detection of two or more types of biological materials using two or more types of magnetic particles.

In one embodiment, the multiplexed detection may include reading the magnetic particles labeled with length, diameter, thickness, shape, color or identification codes so as to be distinguished from each other.

In one embodiment, the method may further include providing 2 to 10 wash wells between the second well and the third well and sequentially immersing the magnetic particle-biological material-detection probe complexes in the wash wells to wash the complexes.

In one embodiment, the magnetic particle-biological material-detection probe complexes may be immersed and transferred for washing using an external magnetic force.

In one embodiment, the method may be designed for diagnosis within less than 30 minutes.

In one embodiment, the method may be carried out through a POCT process.

Effects of the Invention

The POCT diagnostic system for traumatic brain injuries and infectious diseases according to the present invention has a higher magnetism than existing magnetic particles (especially magnetic beads). Therefore, the POCT diagnostic system of the present invention can be mixed or moved using a magnet with high efficiency and can be prepared at a low cost, enabling the same diagnosis at a low cost compared to existing diagnostic systems using magnetic particles.

In addition, the POCT diagnostic system for traumatic brain injuries and infectious diseases according to the present invention includes capture probes having different lengths capable of binding to various biomarkers, enabling simultaneous diagnosis of the biomarkers. Therefore, the point-of-care test (POCT) diagnostic method of the present invention can be used to diagnose target diseases in a short time.

BRIEF DESCRIPTION OF THE DRAWINGS

FIG. 1 shows a diagnostic system using magnetic particles according to one embodiment of the present invention and a process flow diagram of a diagnostic method according to one embodiment of the present invention.

FIG. 2 shows a method for preparing magnetic micro rods according to one embodiment of the present invention.

FIG. 3 shows microscopy images showing the dimensions (including diameter and length) of magnetic micro rods according to one embodiment of the present invention.

FIG. 4 shows a chemical process for treating the surface of a magnetic microrod according to one embodiment of the present invention.

FIG. 5(*a*) and FIG. 5(*b*) show a change in fluorescence from magnetic particles before and after surface treatment according to one embodiment of the present invention: (a) image of magnetic particles whose surface was untreated with an acidic solution and (b) image of magnetic particles whose surface was treated with an acidic solution.

FIG. 6(*a*), FIG. 6(*b*), FIG. 6(*c*) and FIG. 6(*d*) compare the surface of magnetic micro rods according to one embodiment of the present invention with the surface of conventional magnetic beads: (a) surface of magnetic micro rods according to the present invention, (b) schematic of light emission from a magnetic microrod according to the present invention, (c) surface of conventional magnetic beads, and (d) schematic of light emission from a conventional magnetic bead.

FIG. 7(*a*) and FIG. 7(*b*) show optimization results of magnetic micro rods according to one embodiment of the present invention: (a) images showing changes in luminescence with increasing silanization time and (b) graph showing experimental results obtained at different silanization times.

FIG. 8 shows length coding systems including magnetic micro rods for multiplexed detection according to exemplary embodiments of the present invention.

FIG. 9 schematically shows an antigen-antibody reaction between a magnetic microrod and a marker (antigen) according to one embodiment of the present invention.

FIG. 10 shows a process for mixing, heating, and washing using a magnetic bar and a heating block to promote immune reactions.

FIG. 11(*a*), FIG. 11(*b*), FIG. 11(*c*) and FIG. 11(*d*) show images and fluorescence signals detected by an ultrasensitive fluorescent image analyzer according to one embodiment of the present invention: (a) image of magnetic micro rods according to one embodiment of the present invention, (b) fluorescent image according to one embodiment of the present invention, (c) fluorescent image of magnetic micro rods detected by an analysis system of the present invention, and (d) fluorescent images taken by an existing analysis system.

FIG. 12 shows fluorescent images of three or more biomarkers detected using a length coding system including magnetic micro rods according to one embodiment of the present invention and the results of multiplex assay for the biomarkers.

FIG. 13 shows images showing the results of experiments conducted at GFAP concentrations of 0 to 500 pg/ml according to one embodiment of the present invention.

FIG. 14 is a graph showing the results of experiments conducted at GFAP concentrations of 0 to 500 pg/ml according to one embodiment of the present invention.

FIG. 15 shows images showing the results of experiments conducted at UCH-L1 concentrations of 0 to 500 pg/ml according to one embodiment of the present invention.

FIG. 16 is a graph showing the results of experiments conducted at UCH-L1 concentrations of 0 to 500 pg/ml according to one embodiment of the present invention.

FIG. 17(*a*) and FIG. 17(*b*) show a graph and images showing the results of experiments conducted at GFAP concentrations of 0 to 2.5 pg/ml according to one embodiment of the present invention.

FIG. 18(*a*) and FIG. 18(*b*) show images showing the results of multiplexed detection for GFAP (on 300 μm magnetic particles) and UCH-L1 (on 400 μm magnetic particles) according to one embodiment of the present invention: (a) results for GFAP and (b) results for UCH-L1.

FIG. 19 and FIG. 20 are images and a graph showing the results of experiments conducted at IFN-γ concentrations of 0 to 1000 pg/ml according to one embodiment of the present invention.

FIG. 21 is a graph showing the results of experiments conducted at IFN-γ concentrations of 0 to 2.5 pg/ml according to one embodiment of the present invention.

MODE FOR CARRYING OUT THE INVENTION

Preferred embodiments of the present invention will now be described in detail. In the description of the present invention, detailed explanations of related art are omitted when it is deemed that they may unnecessarily obscure the essence of the present invention. Throughout the specification, when a certain portion "comprises" or "includes" a certain component, this indicates that the other components are not excluded and may be further included, unless the context specifically requires otherwise.

As the present invention allows for various changes and numerous embodiments, particular embodiments will be illustrated in drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention.

The present invention is not limited to the illustrated embodiments and may be embodied in various different forms. Rather, the disclosed embodiments are provided so that this disclosure will be thorough and complete, and will fully convey the scope of the invention to those skilled in the art. In the drawings, the dimensions, such as widths and thicknesses, of elements may be exaggerated for clarity. The drawings are explained from an observer's point of view. It will be understood that when an element is referred to as being "on" another element, it can be directly on the other element, or one or more intervening elements may also be present therebetween. It will be understood by those skilled in the art that various changes in form and details may be made therein without departing from the spirit and scope of the invention as defined by the appended claims. The same reference numerals represent substantially the same elements throughout the drawings.

The terms used herein are merely used to describe particular embodiments and are not intended to limit the present invention. As used herein, the singular forms "a", "an" and "the" are intended to include the plural forms as well, unless the context clearly indicates otherwise. In the present invention, it is to be understood that the terms such as "including" or "having," etc., are intended to indicate the existence of the features, numbers, steps, operations, actions, components, parts, or combinations thereof disclosed in the specification, and are not intended to preclude the possibility that one or more other features, numbers, steps, operations, actions, components, parts, or combinations thereof may exist or may be added.

On the other hand, terms used herein are to be understood as described below. While such terms as "first" and "second," etc., may be used to describe various elements, such elements must not be limited to the above terms. The above terms are used only to distinguish one element from another. For example, a first element may be referred to as a second element, and likewise a second element may be referred to as a first element.

As used herein, the singular forms "a", "an" and "the" are intended to include the plural forms as well, unless the context clearly indicates otherwise. In the present invention, it is to be understood that the terms such as "including" or "having," etc., are intended to indicate the existence of the features, numbers, steps, operations, actions, components, parts, or combinations thereof disclosed in the specification, and are not intended to preclude the possibility that one or more other features, numbers, steps, operations, actions, components, parts, or combinations thereof may exist or may be added. Respective steps of the methods described herein may be performed in a different order than that which is explicitly described. In other words, the respective steps may be performed in the same order as described, substantially simultaneously, or in a reverse order.

As used herein, the term "and/or" encompasses both combinations of the plurality of related items disclosed and any item from among the plurality of related items disclosed. In the present specification, the description "A or B" means "A", "B", or "A and B."

The present invention is directed to magnetic particles including a core including a magnetically responsive metal, a shell layer surrounding the core and having a uniform thickness, and capture probes introduced onto the shell layer to capture biological materials, wherein each of the capture probes includes an antibody against a biomarker for the diagnosis of a traumatic brain injury or infectious disease as an antigen.

The core may include a magnetically responsive metal, preferably a magnetic metal or a metal alloyed with a magnetic metal. The magnetic metal may be an alloy with iron (Fe), nickel (Ni), cobalt (Co) or manganese (Mn). The magnetically responsive metal may essentially include at least one transition metal such as iron, nickel, cobalt or manganese and may optionally include at least one rare earth metal such as gadolinium (Gd), terbium (Tb) or samarium (Sm). The magnetically responsive metal may optionally further include one or more other elements such as boron (B), silicon (Si), and carbon (C). The magnetically responsive metal is typically an iron or cobalt alloy. Specifically, the iron alloy is $Fe_{70}B_{15}Si_{10}C_5$ and the cobalt alloy is $Co_{68}Mn_7Si_{10}B_{15}$. The core may include a mixture or alloy of the magnetic metal with copper (Cu), gold (Au), silver (Ag), iron (Fe) or platinum (Pt). More preferably, the core includes a superparamagnetic metal. The core does not directly have magnetism but may be magnetized by an approaching magnet and have an attractive force with the magnet. Accordingly, the use of a magnet is useful for moving and mixing the magnetic particles. In the present invention, it is preferable to use a paramagnetic material rather than a ferromagnetic material. The use of a paramagnetic material for the core reduces the aggregation of the magnetic particles caused by a magnetic attractive force between the magnetic particles when the magnet is removed. The use of a ferromagnetic material leads to aggregation of the magnetic particles, making it difficult to individually observe fluorescence. It is thus preferable to use a ferromagnetic material for the core. Preferably, the magnetic particles have a size and specific gravity such that they are not suspended in water. Due to these physical properties, the magnetic particles can be quickly collected or separated by an external magnet such as a permanent magnet or electromagnet.

The core may occupy 60% or more of the total volume of the magnetic particles. For example, the core may occupy 60 to 99%, preferably 75 to 99%, of the total volume of the magnetic particles. Preferably, the magnetic particles have a size (e.g., a diameter or length) of about several tens to several hundreds of micrometers (μm) and a specific gravity of at least 5, for example, 5 to 30. If the magnetic particles are nanoparticles having a size of less than 1 micrometer, they may be suspended in water despite their high specific gravity (for example, 7.876 for iron nanoparticles). In this case, during a bioassay for detecting biological materials in a well using the magnetic particles under the influence of an applied magnetic field, the biological materials are difficult to separate because the low magnetic force of the microparticles makes control over the magnetism of the magnetic particles difficult. When a magnetic bar is moved up and down in wells to promote immune reactions, microparticles are attached and detached to and from the magnetic bar. Even after the magnetic field is removed, the microparticles attached to the magnetic bar do not fall off on the well bottom and remain non-specifically bound to the magnetic bar during upward and downward movement of the magnetic bar due to their small weight, causing poor reproducibility of quantitative analysis when biological materials present in the wells are detected.

In the magnetic particles of the present invention, the core including the magnetically responsive metal and the shell layer surrounding the core form a core-shell structure. The shell layer may be formed of an organic or inorganic material, preferably glass.

The glass may be composed essentially of at least one compound selected from the group consisting of soda lime, borosilicate, aluminosilicate, silica, alkali silicate, Pyrex, and quartz. Preferably, the glass is borosilicate glass, which is suitable for experiments where heat resistance, acid resistance, and water resistance are required and can minimize non-specific binding to antibodies.

The shell surface may include hydrophilic functional groups.

The capture probes can bind to the shell surface including functional groups, which will be described later. The functional groups are hydrophilic functional groups. The hydrophilic functional groups may be silanol groups or carboxyl, amino, hydroxyl, thiol or aldehyde groups derived from silanol groups. The hydrophilic functional groups are more preferably silanol groups.

The hydrophilic functional groups may be directly bound to the capture probes. Preferably, the hydrophilic functional groups are bound to the capture probes via linkers. The linkers are located between the hydrophilic functional groups and the capture probes to facilitate attachment of the capture probes to the shell layer. Each linker is preferably a silane compound, more preferably an amino-silane, most preferably 3-aminopropyltrimethoxysilane (APTES).

Preferably, the silane compound has a structure represented by $H_2N\text{-}L\text{-}Si(OR)_3$ wherein L is $C_1$-$C_{12}$ alkylene, $C_6$-$C_{20}$ arylene or any combination of the alkylene and the arylene and R is hydrogen or $C_1$-$C_8$ alkyl. The backbone of L may be partially substituted with 0 to 4-NH— moieties.

The silane compound is preferably an amino-silane. Specifically, the amino-silane may be selected from the group consisting of 3-aminopropyltriethoxysilane, aminosilane hydrolysate, 3-aminopropyltrimethoxysilane, 2-aminoethyl-3-aminopropyltrimethoxysilane, 2-aminoethyl-3-aminopropyltriethoxysilane, 2-aminoethyl-3-aminopropylmethyldimethoxysilane, 3-aminopropylmethyldiethoxysilane, 3-aminopropyltrimethoxysilane, N-2-aminoethyl-3-aminopropyltriethoxysilane, triethoxysilylpropyldiethylenetriamine, bis(trimethoxysilypropyl)amine, bis(triethoxysilypropyl)amine, and mixtures thereof. 3-Aminopropyltrimethoxysilane (APTES) is preferred from an economic viewpoint. In one embodiment, the terminal amine group may be converted to a carboxyl group for easy binding to the capture probes.

The shell layer may substantially completely surround the magnetic particles. Alternatively, the surface of the microparticles may not be completely covered with the shell layer and may be partially exposed during production of the microparticles.

The core-shell structure may be formed by applying a liquid shell component to the core metal or filling the core metal component in a hollow frame.

The shell layer may be formed by solidification of an organic or inorganic coating solution. More specifically, the shell layer may be formed by melting an organic or inorganic shell component at a high temperature to make the shell component flowable. Alternatively, the shell layer may be formed by dissolving a shell component in a solvent to prepare a coating liquid and applying the coating liquid to the core metal. The organic material is usually a polymer and the inorganic material may be a metal or a ceramic material, especially glass. For example, the shell layer may be formed by dissolving a plastic material in a solvent or melting glass to obtain a coating solution and applying the coating solution to the magnetic particles by a suitable coating process such as dip coating or spray coating.

The capture probes introduced onto the shell layer serve to capture biological materials. Each of the capture probes includes an antibody against a biomarker for the diagnosis of a traumatic brain injury as an antigen.

ELISA or CT systems for TBI diagnosis are not available in many small and medium-sized hospitals. Even if available, ELISA requires an average of 2 to 3 days for TBI diagnosis, making it difficult to properly treat TBI. CT or MRI requires an average of 5 hours for TBI diagnosis but its accuracy is as very low as about 10%, making it difficult to accurately diagnose TBI. In contrast, the TBI diagnostic system of the present invention is small enough to be applicable to small and medium-sized hospitals and requires low labor and space costs. The TBI diagnostic system of the present invention requires an average of 20 to 30 minutes for diagnosis and has an accuracy as very high as about 98%. Due to these advantages, the TBI diagnostic system of the present invention is very useful for quick and accurate TBI diagnosis.

FIG. 1 shows a diagnostic system of the present invention and a process flow diagram of a diagnostic method using the diagnostic system. Primary antibodies capable of specific binding to TBI biomarkers are immobilized onto surface-modified magnetic particles. The magnetic particles are more improved non-spherical/asymmetric microparticles having a structure in which a magnetic metal is coated with glass and can be distinguished by their length. Immune reactions may occur between the primary antibodies of the magnetic particles and the TBI biomarkers. Since binding processes of such immune reactions cannot be directly observed, labels capable of generating measurable signals may be used. In the present invention, secondary antibody-marker conjugates may be used as the labels. The secondary antibodies are antibodies capable of specific binding to TBI biomarkers and the markers may generally include a fluorescent material or an enzyme.

The magnetic particles of the present invention can be used for the diagnosis of infectious diseases. Infectious diseases are caused by foreign pathogens rather than human cells. When infectious diseases occur, the human body produces antibodies to fight them. For efficient antibody production, the body secretes cytokines such as IL-10 and interferon gamma (IFN-γ). Accordingly, the use of such cytokines or pathogens as biomarkers and antibodies against the pathogens as capture probes enables the diagnosis of infectious diseases in the same manner as described for the TBI diagnosis. Particularly, infectious diseases express very fast symptoms. Some infectious diseases have symptoms fatal to humans. Such infectious diseases need to be rapidly diagnosed and treated. According to a conventional diagnostic method, infectious diseases are primarily diagnosed by observing the expression of symptoms and are finally diagnosed by microscopic observation or PCR and flow cytometric diagnosis. However, such a diagnostic method takes a considerable amount of time to complete the diagnosis, and as a result, appropriate treatment cannot be given to the patients. In contrast, the use of the magnetic particles according to the present invention enables simultaneous diagnosis of multiple infectious diseases with high accuracy and accurate identification of infectious diseases in a short time to provide appropriate treatment for the patients.

Examples of the pathogens include bacteria, spirochetes, rickettsia, viruses, fungi, and parasites. The pathogens can be directly used as biomarkers, but their tissue extracts, cell lysates, proteins, DNAs, and RNAs can also be used as biomarkers. Invasion of the pathogens induces antigen-antibody reactions in the human body. Therefore, antibodies against the pathogens can be used as biomarkers.

The magnetic particles of the present invention have very high surface uniformity. Conventional particles for bioassay are prepared by growing a silica precursor such as TEOS on the surface of core particles to form a shell layer. In this case, the surface of the shell layer is very rough, and as a result, non-specific binding of the particles to target materials occurs frequently, causing unnecessary background noise.

The shell layer may be formed without curvature or protrusions by surface treatment with an acidic material, preferably a mixture of a strong acid and hydrogen peroxide. The mixture of a strong acid and hydrogen peroxide is called a "piranha solution". The traditional piranha solution is a mixture of sulfuric acid and hydrogen peroxide in a ratio of 3:1 to 7:1. The strong acid/hydrogen peroxide mixture is a solution having strong oxidizing power. The strong acid/hydrogen peroxide mixture removes foreign matter present on the shell layer by oxidation and removes protrusions formed on the surface of the shell layer by etching, and as a result, the surface roughness of the shell layer can be minimized to prevent the adhesion of unwanted fluorescent materials. The acidic material may form hydrophilic functional groups on the surface of the shell layer. Linkers or capture probes can be easily bound to the surface of the shell layer through the hydrophilic functional groups, as described above.

1 to 80 hydrophilic functional groups per unit area ($nm^2$) may be introduced onto the shell surface.

Since the linkers or capture probes bound with the hydrophilic functional groups on the shell layer are attached to the magnetic particles, the number of the bound linkers or capture probes may be determined depending on the number of the hydrophilic functional groups. Thus, the formation of the plurality of hydrophilic functional groups on the surface of the magnetic particles allows a large number of the linkers or probes to be attached to the surface of the magnetic particles (FIG. 5). If the density of the hydrophilic functional groups is less than $1/nm^2$, low fluorescence may be observed, which is difficult to measure. Meanwhile, if the density of the hydrophilic functional groups exceeds $80/nm^2$, no further increase in fluorescence may be observed due to interference between the probes bound with the hydrophilic functional groups.

When the capture probes are directly bound to the silanol groups, the hydrophilic functional groups may have a density of 1 to $80/nm^2$. As shown in FIG. 4, the linker is bound with three silanol molecules. In this case, when the hydrophilic functional groups are bound to the capture probes via the linkers, they have a density of 1 to $30/nm^2$.

The surface of the shell layer may be treated with an acidic material. When the shell layer is made of glass, silanol groups as the hydrophilic functional groups present on the glass surface may be bound to the probes. In this case, however, only a small number of capture probes may be attached to the surface of the shell layer, resulting in a low fluorescence intensity. In the present invention, a mixture of sulfuric acid and hydrogen peroxide, called a "piranha solution", is preferably used as the acidic material to form hydrophilic functional groups on the surface of the shell layer. The hydrophilic functional groups formed by the acidic material may be silanol groups or carboxyl, amino, hydroxyl, thiol or aldehyde groups derived from silanol groups. The hydrophilic functional groups are more preferably silanol groups.

The hydrophilic functional groups may be formed by a dry process such as oxygen plasma, corona or UV ozone treatment but are preferably formed by a wet process using an acidic material that is not affected by magnetism while enabling uniform formation of the hydrophilic functional groups on the surface of the magnetic micro rods. That is, the surface of the shell layer is treated with an acidic material, particularly a piranha solution for oxidative hydrophilization to greatly increase the number of active sites (hydrophilic functional groups) with which the probes can be bound, resulting in a high fluorescence intensity (see FIG. 5).

Glass (for example, borosilicate glass) for the shell layer exhibits little non-specific binding caused by adsorption with a reaction sample through a chemical reaction. Particularly, the surface of the magnetic particles is very uniform because the shell layer has a coating layer derived from a liquid component. The average surface roughness ($R_a$) of the shell layer may be 15 nm or less, preferably 10 nm or less, more preferably 5 nm or less, more preferably 2 nm or less, particularly 1.5 nm or less. The $R_a$ may be, for example, 3 nm or more, 2 nm or more or 1 nm or more. If the surface roughness exceeds 15 nm, non-specific adsorption of a fluorescent material on the surface of the shell layer may increase, resulting in increased noise during fluorescence observation.

The thickness of the shell layer may be 1 to 100 μm, preferably 1 to 50 μm, more preferably 1 to 10 μm, and even more preferably 4 to 8 μm. If the thickness of the shell layer is less than the lower limit, the surface of the shell layer tends to be brittle or is apt to crack. Meanwhile, if the thickness of the shell layer exceeds the upper limit, problems may be caused by the characteristics and wavelength of a laser during glass cutting.

The magnetic particles may have a limit of detection of 1 pg/ml or less and a dynamic range of at least log 3. The use of the magnetic particles enables fluorescence analysis even at a concentration of 0.625 pg/ml, as shown in FIG. 17. Accordingly, the magnetic particles of the present invention have a limit of detection of 1 pg/ml or less, preferably 0.7 pg/ml or less, most preferably 0.625 pg/ml or less. The limit of detection may be, for example, at least 0.001 pg/ml, at least 0.01 pg/ml or at least 0.1 pg/ml. As shown in FIGS. 19 and 20, the magnetic particles have a dynamic range of at least log 3, preferably at least log 5. For example, the dynamic range may be log 3 to log 10, preferably log 5 to log 7. As shown in FIGS. 14 and 16, as the concentration increases in the range of 0 to 500 pg/ml, the fluorescence signal increases, demonstrating a very high correlation therebetween (coefficient of determination, $R^2$: 0.9895). In conclusion, the use of the magnetic particles according to the present invention leads to a ~40-fold increase in sensitivity compared to the use of conventional magnetic particles. When optimized, the magnetic particles of the present invention may have at least 100-fold higher sensitivity than conventional magnetic particles.

The magnetic particles may have two or more different lengths and may diagnose two or more types of biomarkers simultaneously. In this case, the magnetic particles may be bound with different capture probes depending on their lengths (FIG. 8). As a result, different fluorescence lengths are generated depending on the capture probes, enabling simultaneous diagnosis of two or more types of biomarkers. For this purpose, the magnetic particles may have 2 to 20 different lengths that differ by 5 to 200 μm. The use of the magnetic particles having various lengths enables simultaneous detection of 2 to 20 types of biomarkers. If the lengths of the magnetic particles are different by less than 5 it may be difficult to distinguish the length differences using an optical system. Meanwhile, if the lengths of the magnetic particles are different by more than 200 μm, it is easy to distinguish the length differences but it may be difficult to use a number of lengths of the magnetic particles, making it difficult to simultaneously identify multiple types of biomarkers.

As an example, an antibody capable of reacting with GFAP may be coupled as a capture probe on the surface of the magnetic particles having a length of 300 μm and an antibody capable of reacting with UCH-L1 may be coupled as a capture probe on the surface of the magnetic particles having a length of 400 μm. When the magnetic materials having different lengths are used, the same fluorescence is generated but whether the biomarker is GFAP (fluorescence length 300 μm) or UCH-L1 (fluorescence length 400 μm) can be read due to the difference in length of the magnetic materials, indicating that the types of the biomarkers can be accurately determined by simple optical observation even without the need for gene testing such as PCR.

This can be extended to the magnetic particles having a larger number of different lengths. For example, when the magnetic particles have 10 different lengths and are coupled with capture probes, 10 types of biomarkers can be identified simultaneously. However, when the magnetic particles have 20 or more different lengths, the number of the magnetic particles corresponding to each length is insufficient, failing to obtain adequate fluorescence. Thus, a large amount of the magnetic particles should be used to obtain sufficient fluorescence, inevitably resulting in poor efficiency.

The magnetic particles may be obtained by cutting glass-coated metal micro wires. Various lengths of the magnetic particles may be obtained simply by cutting glass-coated metal micro wires to different lengths with a laser.

The magnetic particles may be in an unshaped or shaped form. When shaped, the magnetic particles are in the form of rods, sheets or spheres. The sheet-like magnetic particles may have various cross-sectional shapes such as stars, polygons, and circles but are not particularly limited thereto. The magnetic particles are in the form of micro rods, micro discs or micro beads, which are preferable in terms of convenience of production and ease of observation. The magnetic particles are particularly preferably in the form of micro rods. The magnetic particles in the form of micro rods are easy to distinguish from each other due to their overlap. When placed in wells, the magnetic particles in the form of micro rods are easy to focus on. Since the individual particles in the form of micro rods occupy small areas, a large number of the microparticles can be displayed on a single screen. The magnetic particles may have complex cross-sectional shapes such as stars. In this case, however, the magnetic particles tend to collide with each other or with the walls of the wells while moving in the wells, causing breakage at the edges. Therefore, it is advantageous that the magnetic particles have simple shapes such as micro rods.

The micro rods may have a length of 10 to 1,000 μm. If the micro rods have different lengths less than the lower limit, they are not easy to distinguish from each other and are difficult to mix, wash, and move using a magnet due to their reduced magnetism. Meanwhile, if the length of the micro rods exceeds the upper limit, the particles may overlap, making their observation difficult, and it is difficult to introduce a desired amount of the magnetic particles into one well, posing a difficulty in diagnosis. The ratio of the length to the diameter (i.e. aspect ratio) of the micro rods may be at least 2, at least 5 or at least 10 and may be 20 or less. If the aspect ratio is less than 2, the micro rods are close to spherical microparticles, making it difficult to distinguish from each other. Meanwhile, if the aspect ratio exceeds 20, the reduced diameter of the magnetic particles leads to a relatively small thickness of the magnetic core, resulting in low magnetism. Further, the reduced diameter of the magnetic particles leads to poor durability, resulting in breakage of the magnetic particles during testing.

The magnetic particles can be suitably used for in vitro diagnostics for detecting biological materials in sample solutions derived from living organisms. The sample solutions may be tissue extracts, cell lysates, whole blood, plasma, serum, saliva, ocular humor, cerebrospinal fluid, sweat, urine, milk, ascites fluid, synovial fluid, and peritoneal fluid. For rapid diagnosis, the pretreatment of the sample solutions may be simplified or may be even omitted.

The biological materials may be biomarkers, blood, plasma, serum, body fluids, proteins, peptides, nucleic acids, bacteria, viruses, endoplasmic reticula, miRNAs, exosomes, and circulatory tumor cells. Preferably, the biological materials are biomarkers. In particular, the magnetic particles of the present invention are very useful for biomarker detection due to their ability to detect various types of biological materials in a single test to quickly and early diagnose diseases. The biomarkers are not limited as long as they are used in general scientific or medical applications for the measurement or evaluation of biological treatment, pathogenesis, and pharmacological treatment processes. The biomarkers may be, for example, polypeptides, peptides, nucleic acids, proteins or metabolites that can be detected in biological fluids such as blood, saliva, and urine. Specifically, the biomarkers may be used without limitation as long as their blood concentration increases where a traumatic brain injury occurs. Examples of preferred biomarkers include glial fibrillary acidic protein (GFAP), ubiquitin C-terminal hydrolase-1 (UCH-L1), S100, and Tau protein. The biomarkers show a tendency to increase not only in patients with general TBIs (mTBIs) but also in patients with mild traumatic brain injuries (TBIs). Therefore, the magnetic particles of the present invention can be used to diagnose not only severe patients with clear TBI symptoms but also mild patients with TBI symptoms.

In one embodiment of the present invention, the capture probes may be introduced onto the shell layer to capture the biological materials in the sample solutions. The capture probes allow the biological materials to be captured by the magnetic particles due to their ability to specifically bind to the biological materials. The capture probes may be antibodies, proteins, nucleic acids or aptamers. For example, the capture probes may be capture antibodies capable of specific binding to the biomarkers to capture the biomarkers. The capture probes may be immobilized on the surface of the magnetic particles by adsorption or chemical bonding. Preferably, the capture probes are linked to hydrophilic functional groups present on the surface of the shell layer. For example, the capture probes may be attached to the magnetic particles by introducing biotin on the surface of the capture probes and introducing avidin, neutravidin or streptavidin capable of binding to biotin onto the magnetic particles. Alternatively, the capture probes may be linked to the magnetic particles via hydrophilic functional groups on the surface of the magnetic particles.

The hydrophilic functional groups may be directly bound to the capture probes. Preferably, the hydrophilic functional groups are bound to the capture probes via linkers. Each linker may be a silane compound, as described above (see FIG. 4).

The present invention will now be described in detail based on a method for preparing magnetic particles.

The present invention is also directed to a method for preparing magnetic particles for detecting biological materials, including (i) preparing magnetic micro rods consisting of a shell made of glass and a core including a magnetic material, (ii) treating the surface of the magnetic micro rods with an acidic solution to form silanol groups, (iii) immersing the surface-treated magnetic micro rods in a silane-based solution to bind a silane compound to the silanol groups, (iv) converting the terminal groups of the silane molecules to terminal groups capable of binding to probes, and (v) attaching probes to the terminal groups of the silane molecules.

In step (i), magnetic micro rods consisting of a shell made of glass and a core including a magnetic material are prepared.

Specifically, the magnetic micro rods are prepared by filling a metal powder in a glass tube, drawing glass-coated micro wires from the filled glass tube under heating, and cutting the micro wires to uniform lengths (see FIG. 2). This process is based on the Talyor-Ulitovsky technique whose basic principle is described, for example, in WO1993/005904 A2, which is herein incorporated by reference.

The preparation of the glass-coated micro wires will be explained in more detail. First, a metal (magnetic particles) is filled in a glass tube and the filled glass tube is placed in a heating unit heated by a heating means. The metal may be in the form of a powder or may be a compound that forms a metal when melted. A molten metal may be directly filled in the glass tube. The metal powder has an average particle diameter of 40 to 300 μm, preferably 50 to 200 μm, more preferably 70 to 150 μm. If the average particle diameter of the metal powder is less than 40 μm, the metal powder may be scattered in the air during processing and the price of the powder may increase, leading to an increase in the overall production cost. Meanwhile, if the average particle diameter of the metal powder exceeds 300 μm, a smooth transfer of the metal powder to the glass tube may not be ensured, and as a result, the resulting micro wires may have empty spaces in which the metal does not exist, causing the formation of defects (FIG. 3).

The glass tube has an inner diameter of 0.2 to 2 mm, preferably 0.3 to 1.5 mm, more preferably 0.5 to 1 mm. If the inner diameter of the glass tube is less than 0.2 mm, the metal constituting the core may not be easily filled in the glass tube. Meanwhile, if the inner diameter of the glass tube exceeds 2 mm, the relative diameter of the core may increase, and as a result, the glass shell layer may become thin during drawing, causing poor durability or the formation of curvature or protrusions on the surface (FIG. 3).

The glass tube may be made of soda lime, borosilicate, aluminosilicate, silica, alkali silicate, Pyrex or quartz. Alternatively, the glass tube may be produced by processing glass containing lead oxide, tellurium dioxide or silica as a major component into a tube. The softening point of the glass is in the range of about 1,000 to about 1,900° C., preferably about 1,100 to about 1,700° C. If the softening point of the glass is lower than 1,000° C., the glass tube may be softened before melting of the metal powder, causing the formation of defects. Meanwhile, if the softening point of the glass exceeds 1,900° C., a long time and a high cost are needed for heating, which is economically unfavorable.

The glass (for example, borosilicate glass) for the shell layer exhibits little non-specific binding caused by adsorption with a reaction sample through a chemical reaction, minimizing the occurrence of noise.

It is preferable that the metal has a melting temperature lower than the softening point of the glass tube. If the melting temperature of the metal is higher than the softening point of the glass, the metal powder may not be melted during drawing and may remain in the glass tube, and as a result, the metal powder may leak out during use, deteriorating the lifetime of the magnetic particles and causing contamination with foreign matter.

The heating means may be arranged under the glass tube or at a position adjacent to the glass tube to heat the glass tube to the softening point at which the glass tube can be drawn out.

The metal powder forms droplets during heating and the glass tube adjacent to the metal powder is softened to surround the droplets formed from the metal powder. Specifically, since the glass tube is softened and drawn out simultaneously with the melting of the metal powder filled in the glass tube, the core of the magnetic particles is drawn out while being coated with the glass.

The heating means may be, for example, an induction heater known in the art, specifically an inductor. For example, spiral coils (e.g., copper coils) may be wound in the inductor. Specifically, a heating region may be formed in the coils. The number of the coils may be selected in consideration of the desired height of the molten metal, etc. The heating region is heated by the eddy-current loss generated by a magnetic field at the required frequency. The heating means may be a high-frequency inductor, where the frequency may be, for example, about 0.5 to about 800 kHz, specifically about 10 to about 500 kHz, but is not limited thereto.

The internal temperature of the heating region is preferably 1,000 to 2,000° C., at which the glass tube can be softened, and may vary depending on the material for the glass tube and the type of the metal constituting the core of the magnetic particles.

As described above, the magnetic particles filled in the glass tube may include copper (Cu), gold (Au), silver (Ag), iron (Fe) or platinum (Pt), more preferably a superparamagnetic metal.

In this connection, a cobalt alloy or an iron-rich alloy may be mentioned as a representative example of the magnetic metal. In a specific embodiment, a small amount (e.g., up to about 5 atomic %, specifically up to about 3 atomic %) of copper may be added to or incorporated into the magnetic metal to increase the number of nucleation centers and promote nanocrystallization.

After the heating is finished, the molten metal constituting the core of the micro wires in the glass tube is filled in glass capillaries and is drawn.

The interior of the glass tube may be in an inert gas atmosphere, for example, helium, neon, argon or nitrogen gas atmosphere, during drawing. The replacement of the atmosphere of the glass tube with an inert gas atmosphere can prevent oxidation of the magnetic particles during melting.

The drawing results in the formation of micro wires in which the metal core is substantially completely coated with glass. The drawn micro wires can be solidified while being cooled by a cooling means arranged at the rear end of the heating means.

Any cooling means that can heat the micro wires may be used without limitation. The cooling means may use a coolant in which the micro wires are immersed for cooling. The coolant may be water, oil or a refrigerant but is preferably water.

As described above, the solidified micro wires are recovered by a take-up machine mounted in the system. The take-up machine may have a coil shape. Specifically, the take-up machine is of a wire bobbin type.

In the glass-coated metal micro wires, the diameter of the core metal is in the range of 30 to 100 μm, preferably 40 to 80 μm, more preferably 50 to 70 μm. The thickness of the glass coating (shell layer) is in the range of 3 to 50 μm, preferably 5 to 20 μm, more preferably 7 to 15 μm. The entire diameter of the micro wires may be, for example, about 30 to 120 μm, preferably 30 to 100 μm, more preferably 40 to 80 μm.

The micro wires including the magnetic material may be continuously produced to a length of 1 to 15 km, preferably 5 to 10 km, on the take-up machine and packaged in a roll form. The micro wires can be used to prepare non-spherical micro rods, as will be described later.

The micro wires can be cut to predetermined lengths to prepare non-spherical magnetic micro rods. More specifically, the micro wires are arranged in the transverse direction (e.g., in parallel) and cut to predetermined lengths to prepare a large amount of non-spherical/asymmetrical microparticles. A laser is used in a non-contact mode for cutting.

Specifically, the micro wires can be cut by the method disclosed in Korean Patent Publication No. 2018-0130436. More specifically, the micro wires can be prepared by a method including: preparing a wire holder having a plurality of grooves arranged in the transverse direction and positioning the glass-coated metal micro wires in the individual grooves of the wire holder; and cutting the glass-coated metal micro wires positioned in the wire holder at predetermined intervals in the traverse direction using a laser in a non-contact mode wherein the laser has a pulse width shorter than the heat propagation time of the glass-coated metal micro wires.

The resulting magnetic micro rods are surface treated with a mixture of a strong acid and hydrogen peroxide to make their surface smooth. The method may further include washing the surface to remove foreign matter present on the surface before the surface treatment.

The washing can be performed using various organic solvents. More specifically, the magnetic particles (magnetic micro rods) are washed with an organic solvent and then the organic solvent is removed using ethanol. The organic solvent is preferably acetone. After treatment with the organic solvent, the magnetic particles are treated with an acid. The acid is preferably sulfuric acid. The acid-treated magnetic particles are cleaned with a mixture of water and ethanol. The acid-treated magnetic particles are treated with a base. The base is sodium hydroxide, preferably a solution of sodium hydroxide in a mixed solvent of water and ethanol. The base-treated magnetic particles are preferably washed with water and ethanol.

In step (ii), the surface of the magnetic micro rods is treated with an acidic solution to form silanol groups.

For example, after completion of the washing, the magnetic particles may be surface treated with an acidic solution.

The acidic solution is preferably a mixture of a strong acid and hydrogen peroxide, for example, a piranha solution. The piranha solution generally refers to a mixture of sulfuric acid and hydrogen peroxide and is intended to include mixtures of sulfuric acid and hydrogen peroxide in various ratios. The typical piranha solution is a solution of sulfuric acid and hydrogen peroxide in a volume ratio of 3:1 to 7:1. Aside from this, a mixture of ammonia water and hydrogen peroxide is called a basic piranha solution.

The acidic solution is preferably a mixture of a strong acid and hydrogen peroxide in a volume ratio of 1:1 to 7:1, more preferably 2:1 to 5:1, most preferably 3:1. If the ratio is less than <1:1, that is, the content of hydrogen peroxide is higher than that of the strong acid, large amounts of heat and gas may be released during the preparation of the acidic solution, increasing the risk of explosion. Meanwhile, if the ratio is >7:1, sufficient oxidation by the piranha solution may not be attained, making it difficult to form silanol groups. The hydrogen peroxide may be a solution of 10 to 50% by volume, preferably 20 to 40% by volume, more preferably 30% by volume of hydrogen peroxide. If a solution of less than 10% by volume of hydrogen peroxide is used, sufficient oxidation by the piranha solution may not be attained, making it difficult to form silanol groups. Meanwhile, if a solution of more than 50% by volume of hydrogen peroxide is used, large amounts of heat and gas may be released during the preparation of the acidic solution, increasing the risk of explosion.

Since the piranha solution is a highly corrosive and strong oxidizing agent, care should be taken in handling. Before using the piranha solution, foreign materials on the surface of a target object need to be completely washed and solvents used for washing must also be removed. The piranha solution can dissolve and remove organic contaminants but large amounts of contaminants or washing solvents may violently generate bubbles or induce explosive reactions to release large amounts of gases.

The piranha solution is preferably prepared by adding hydrogen peroxide to sulfuric acid. The addition of sulfuric acid to hydrogen peroxide generates large amounts of gases and increases the risk of explosion. Even when hydrogen peroxide is added to sulfuric acid, a violent exothermic reaction occurs. It is thus preferable to lower the temperature by appropriate cooling. The content of the hydrogen peroxide is limited to 50% by volume or less, more preferably 30% by volume, to control the violent reaction.

The piranha solution can oxidize the metal surface or the glass surface. Particularly, the piranha solution oxidizes and removes foreign matter and unwanted protrusions on the glass surface and hydrophilizes the glass surface to form a large number of silanol groups.

The acidic solution can convert 1 to 90% of the molecules on the glass surface of the magnetic micro rods to silanol groups. The formation of a large number of silanol groups on the surface of the magnetic micro rods enables the attachment of a large number of probes to the surface of the magnetic particles. That is, the use of the acidic solution to form silanol groups on the surface allows a large number of hydrophilic functional groups or a number of functional groups (linkers) bonded to a silane to bind to the silanol groups (FIG. 5). If the density of the silanol groups is less than $1/nm^2$, low fluorescence may be observed, which is difficult to measure. Meanwhile, if the density of the silanol groups exceeds $80/nm^2$, no further increase in fluorescence may be observed due to interference between probes to be bound with the silanol groups.

When capture probes are directly bound to the silanol groups, the silanol groups may have a density of 1 to $80/nm^2$. As shown in FIG. 4, the linker is bound with three silanol molecules. In this case, when the silanol groups are bound to the capture probes via the linkers, they have a density of 1 to $30/nm^2$.

In step (iii), the surface-treated magnetic micro rods are immersed in a silane-based solution to bind a silane compound to the silanol groups.

After completion of the surface treatment (step (ii)), a silane compound is allowed to react with the shell layer of the magnetic particles. As described above, the silane compound can be attached to the silanol groups formed on the surface of the shell layer via 3-aminopropyltriethoxysilane (APTES). The APTES is preferably in the form of a solution in acetone or toluene. The APTES may be bonded with the silanol groups to form an amino-silane. The reaction time is preferably within 6 to 24 hours. In this case, optimal fluorescence can be detected during subsequent fluorescence analysis. If the reaction time is shorter than 6 hours, the amount of APTES bonded to the silanol groups may be reduced, resulting in low fluorescence intensity. Meanwhile, if the reaction time exceeds 24 hours, it takes a long time to prepare the magnetic particles without any change in fluorescence intensity, resulting in an increase in cost (see FIG. 7).

In step (iv), the terminal groups of the silane molecules are converted to terminal groups capable of binding to probes.

The surface of the shell layer of the magnetic particles on which the amino-silane is formed is preferably substituted with carboxyl, hydroxyl, thiol or aldehyde groups. The capture probes are easily bound with different terminals depending on their types. Thus, the terminal group (amine group) of the amino silane may be converted to a terminal group capable of binding to a probe. When the amino group of the amino-silane (linker) easily binds to the capture probe, it may also be used without conversion.

The amine group of the amino-silane is more preferably converted to a carboxyl group by reaction with γ-butyrolactone or succinic anhydride.

In step (v), probes are attached to the terminal groups of the silane molecules.

The magnetic micro rods may be attached with probes before use. The probes are preferably capture probes. The capture probes are probes that perform antigen-antibody reactions with biomarkers. Biomarkers are attached to the magnetic micro rods through the capture probes. Detection probes may be separately attached to the biomarkers. The biomarkers may be detected by the action of fluorescent materials or enzymes located on the detection probes.

According to another aspect of the present invention, there is provided a method for detecting biological materials using the magnetic particles. The method includes (1) providing the magnetic particles to a first well, (2) transferring the magnetic particles from the first well to a second well using a magnetic force, (3) providing detection probes capable of specific binding to biological materials and conjugated with a luminescent material emitting light in response to an external stimulus to the second well and allowing the capture probes, the biological materials, and the detection probes to react with one another to form complexes of the magnetic particles, the biological materials, and the detection probes, and (4) transferring the magnetic particle-biological material-detection probe complexes to a third well using a magnetic force and measuring luminescence signals generated from the luminescent material present in the complexes in response to the external stimulus to detect the biological materials.

In step (1), the magnetic particles are provided to a first well.

The magnetic particles may be the magnetic micro rods prepared by the above method. The magnetic micro rods may be immersed and stored in the first well.

In step (2), the magnetic particles are transferred from the first well to a second well using a magnetic force.

The magnetic particles can be transferred to the second well using a magnetic force due to their magnetism. The magnetic force is preferably created by a magnetic bar. After the magnetic particles are transferred to the second well using the magnetic bar covered with a cap, the capped magnetic bar is removed. As a result, the magnetic particles may be immersed in the second well or may be suspended in a solvent in the second well. The subsequent transfer of the magnetic particles using magnetism may be performed in the same manner as above.

In step (3), detection probes capable of specific binding to biological materials and conjugated with a luminescent material emitting light in response to an external stimulus are provided to the second well and the capture probes, the biological materials, and the detection probes are allowed to react with one another to form complexes of the magnetic particles, the biological materials, and the detection probes.

Like the capture probes, the detection probes may be antibodies, proteins, nucleic acids or aptamers capable of specific binding to the biological materials. For example, the detection probes may be detection antibodies that specifically bind to the biomarkers and are conjugated with a luminescent material.

The detection antibodies and the capture antibodies of the capture probes may be antibodies against biomarkers for traumatic brain injuries as antigens. For example, any biomarkers whose blood concentration increases where a traumatic brain injury occurs may be used without limitation as the antigens. Examples of preferred biomarkers include glial fibrillary acidic protein (GFAP), ubiquitin C-terminal hydrolase-1 (UCH-L1), S100, and Tau protein. The biomarkers show a tendency to increase not only in patients with general TBIs (mTBIs) but also in patients with mild traumatic brain injuries (TBIs). Therefore, the magnetic particles of the present invention can be used to diagnose not only severe patients with clear TBI symptoms but also mild patients with TBI symptoms.

The luminescent material is bound to the detection probes and generates light in response to an external stimulus to detect the presence of the biological materials. The external stimulus is selected from ultraviolet light, electron beams, chemical reactions, and enzyme-substrate reactions. Examples of suitable luminescent materials include fluorescent molecules, quantum dots, metal nanoparticles, magnetic nanoparticles, enzymes, and enzyme substrates. Particularly, fluorescent molecules are preferred because of their ease of purchase and convenience of application. The fluorescent molecules can be selected from the group consisting of fluorescein isothiocyanate (FITC), fluorescein, fluorescein amidite (FAM), phycoerythrin (PE), tetramethylrhodamine isothiocyanate (TRITC), cyanine 3 (Cy3), cyanine 5 (Cy5), cyanine 7 (Cy7), Alexa Fluor dyes, and rhodamine.

The complexes of the magnetic particles, the biological materials, and the detection probes can be prepared by mixing the magnetic particles immobilized with the capture antibodies, the detection antibodies specifically binding to the biological materials, and a sample solution containing the biological materials in a reaction tube. The complexes can be prepared by simultaneously inducing first immune reactions between the biological materials and the magnetic particles and second immune reactions between the biological materials and the detection antibodies in the reaction tube.

The formation of the complexes may include promoting the reactions in the presence of an external magnetic force. For example, the immune reactions may be promoted by heating the reaction tube on a heating block to an appropriate temperature and allowing a magnetic bar to continuously move up and down in the reaction tube to rapidly mix the immunoreactive materials.

The method may further include washing the complexes in the presence of an external magnetic force. That is, the method may further include continuously washing the complexes of the microparticles, the biological materials, and the detection probes and the magnetic bar in two or more washing tubes after completion of the first and second immune reactions. After the washing, luminescence signals from the complexes are detected to accurately identify the types and amounts of the biological materials.

The method may be carried out using an independent reaction tube, as described above, but preferably uses a multi-well plate. In this case, the magnetic particles may be introduced into a first well of the well plate and may be transferred to a second well of the well plate for testing. The detection probes and the biological particles may be introduced into the second well. Accordingly, the magnetic particles, the detection probes, and the biological particles are allowed to react in the second well to form magnetic particle-biological material-detection probe complexes. The complexes can be transferred to a third well of the well plate for fluorescence measurement.

2 to 10 wash wells may be provided between the second well and the third well. The wash wells are simple wells in which a washing solution is filled. The magnetic particle-biological material-detection probe complexes can be immersed and washed in the wash wells. The washing serves to remove biological materials and detection probes remaining unbound to the magnetic particles. As described above, the magnetic particles of the present invention can minimize the amount of non-specifically bound fluorescent molecules (detection probes), enabling accurate fluorescence measurement. During the washing, the magnetic particle-biological material-detection probe complexes may be immersed and transferred using an external magnetic force in the same manner as in the formation of the complexes.

In step (4), the magnetic particle-biological material-detection probe complexes are transferred to a third well using a magnetic force and luminescence signals generated from the luminescent material present in the complexes in response to the external stimulus are measured to detect the biological materials.

The method of the present invention may be carried out by an immunodiagnostic assay. Particularly, the luminescence signals can be detected by a suitable technique, for example, ELISA or fluorescence measurement.

More specifically, the ELISA technique is carried out by binding the target materials in the sample to the capture antibodies immobilized onto the giant magnetic particles and treating the detection antibodies. The detection antibodies bind to the opposite sides to the sides of the target materials to which the capture antibodies are bound. An enzyme called horseradish peroxidase (HRP) is conjugated to the detection antibodies. The enzyme uses hydrogen peroxide to degrade TMB substrate, giving a color. The chromaticity of the color is determined by the OD value. That is, the method is based on the principle that quantitatively large numbers of the capture antibodies and the detection antibodies are attached in proportion to the amounts of the target materials in the sample, and as a result, the amount of HRP conjugated to the detection antibodies increases, so that the enzymatic reactions proceed relatively rapidly, causing a rapid change in the color of TMB substrate. The amounts of the target materials in the sample can be determined by previously treating with various concentrations of the target materials to obtain OD values, drawing a standard curve from the OD values, treating with the actual sample to obtain OD values, and comparing the actual OD values with the standard curve. At this time, all OD values and concentrations can be calculated with the automatic analysis program of the analyzer.

The fluorescence measurement technique is based on the same principle as the ELISA technique in that the capture antibodies and the detection antibodies are used for sandwich assay, except that biotin is conjugated to the detection antibodies instead of HRP enzyme and is treated with a streptavidin-conjugated fluorescent material to measure fluorescence values. First, TBI protein reacts with and is attached to the capture antibodies, followed by treatment with the detection antibodies conjugated with biotin to attach the detection antibodies to the opposite sides to the sides of the TBI to which the capture antibodies are attached. Thereafter, after treatment with e-flour as the fluorescent material conjugated with streptavidin, fluorescent signals from the magnetic particles are measured. Based on the principle that higher concentrations of the target diagnostic markers lead to stronger fluorescence signals from the magnetic particles, the locations of the magnetic particles in the reaction well are identified with a bright field microscope, and fluorescence signals from the corresponding locations are measured in pixels, and images of fluorescence signals from about 10 microparticles are automatically analyzed. Fluorescence values are measured in the same manner after reaction with various concentrations of the target materials, a standard curve is drawn from the measured fluorescence values, and fluorescence values from the test detection are applied to the standard curve to calculate the concentrations of the corresponding target proteins in the final sample. All images are analyzed and all fluorescence values are calculated with the automatic analysis program of the analyzer.

The method of the present invention may be carried out through a POCT process. POCT is an abbreviation for "Point-Of-Care Test" and refers to a direct test that is carried out in the presence of a patient. In other words, POCT means a test that is not conducted by a medical technologist in an independent space such as a central laboratory of a hospital but is conducted by a doctor, nurse or medical technologist near the patient, for example, in a hospital room, emergency room, operating room or intensive care unit. A conventional diagnostic method for a traumatic brain injury requires a large-scale system such as CT or MM, making it impossible to conduct on-site testing. A conventional immunodiagnostic method requires a large-scale diagnostic system such as an automated CLIA analyzer and is thus limited in its use for on-site diagnosis. In contrast, the method of the present invention can use a miniaturized diagnostic system, enabling on-site diagnosis through a POCT process.

Preferred embodiments of the present invention will be described in detail with reference to the accompanying drawings such that those skilled in the art can readily practice the invention. In describing the present invention, detailed explanations of a related known function or construction are omitted when it is deemed that they may unnecessarily obscure the essence of the invention. Certain features shown in the drawings are enlarged, reduced or simplified for ease of illustration and the drawings and the elements thereof are not necessarily in proper proportion. However, those skilled in the art will readily understand such details.

EXAMPLES

Step 1: Preparation and Surface Treatment of Magnetic Micro Rods

Glass-coated micro wires were produced in accordance with the disclosure of Korean Patent Publication No. 10-2018-0130436. The glass-coated micro wires were cut into magnetic micro rods having appropriate sizes. Preferably, the glass-coated micro wires were cut such that the length was 400 μm, the diameter of the magnetic metal core was 50 μm, and the thickness of the glass coating was 5 μm. Accordingly, the final magnetic micro rods had a diameter of 60 μm and a length of 400 μm.

The magnetic micro rods were washed to remove foreign matter from their surface. The washed magnetic micro rods were placed in a vial, precipitated by adding acetone, washed with ethanol, and dried. The dried magnetic micro rods were immersed in sulfuric acid, washed with water and ethanol, and dried. The acid-treated magnetic micro rods were treated with a sodium hydroxide solution (a mixture of 1 g of NaOH, 4 ml of water, and 6 ml of ethanol) and washed with ethanol.

Next, primary antibodies binding to antigens in a sample were bound to the magnetic micro rods. To this end, the glass surface of the magnetic micro rods was appropriately modified. First, the washed magnetic micro rods were immersed in a piranha solution (a mixed solution of $H_2SO_4$ and 30 vol % of $H_2O_2$ in a 3:1 volume ratio) to modify the surface glass with silanol (Si—OH), washed with water and ethanol, and dried. Thereafter, the surface-modified magnetic micro rods were immersed in 2 vol % of an APTES solution for silanization, washed with toluene, ethanol, and water, and cured at a temperature of 110° C.

The primary antibodies were immobilized onto the micro rods surface modified with the amino-silane. For better immobilization with the primary antibodies, the amino groups were preferably converted to carboxyl groups. In this case, carboxyl beads were produced. Approximately 10,000 micro rods (500×75 μm) could be treated in a 1.5 ml E-tube. Two methods using γ-butyrolactone or a mixture of succinic anhydride and triethylamine could be used for conversion to carboxyl groups. The method using succinic anhydride and triethylamine was judged to be more effective.

Finally, the amino-silane was coated with fluorescein isothiocyanate isomer (FITC) for fluorescence measurement to determine the uniformity and degree of modification. The surface-modified micro rods were found to have a very uniform surface compared to previously known silica (TEOS)-treated magnetic beads (see FIG. 6). Accordingly, non-specific binding of unwanted materials was reduced, resulting in a significant noise reduction. In addition, TBI biomarkers as the antigens could be detected and analyzed and signal amplification effects could be observed even at very low concentrations (<~1 pg/ml).

A large amount of amino-silane were bound to the inventive magnetic particles surface modified with the piranha solution, and as a result, the inventive magnetic particles showed high fluorescence compared to conventional magnetic particles (see (b) of FIG. 5).

Step 2: Preparation of Giant Magnetic Microrod Complexes Immobilized with Primary Antibodies Giant magnetic microrod complexes (rod beads) immobilized with primary antibodies specifically binding to target markers as antigens in a sample solution were prepared using the surface-modified magnetic micro rods (preferably surface modified with carboxyl groups) prepared in step 1. Specifically, the giant magnetic microrod complexes were prepared by the following procedure.

1) Transfer the magnetic micro rods (~2,500/vial) to a new E-tube.
2) Wash the magnetic micro rods once with 500 µl of MES buffer (pH 5.0).
3) Place 400 µl of MES buffer (pH 5.0), 50 mg/ml of EDC, and 50 mg/ml of NHS (total reaction volume 500 µl) in the E-tube containing the magnetic micro rods, followed by slow shaking at room temperature (25° C.) for 30 min (at 30 rpm on a rotary shaker (Rotation machine)).
4) Wash with 500 µl of MES buffer twice (while tapping 30 times).
5) Completely remove the MES buffer from the E-tube.
6) Place 0.1 mg/ml of primary antibodies in IVIES buffer (pH 6.0) in the tube, followed by slow shaking at room temperature for 2 h (at 30 rpm on a rotary shaker (Rotation machine)).
7) Wash with 500 µl of a wash buffer (0.1% BSA, 1×PBS, 0.1% T-20, 0.05% $NaN_3$) twice (while tapping 30 times).
8) Completely remove the wash buffer (0.1% BSA, 1×PBS, 0.1% T-20, 0.05% $NaN_3$) from the E-tube.
9) Add 500 µl of a blocking buffer (1% BSA, 1×PBS, 0.1% T-20, 0.05% $NaN_3$), followed by slow shaking at room temperature for 1 h (at 30 rpm on a rotary shaker (Rotation machine)).
10) Wash with 500 µl of a secondary blocking buffer (10 mM Tris-Cl (pH 8), 1% BSA, 0.1% T-20, 0.05% $NaN_3$, 0.1M NaCl) twice (while tapping 30 times).
11) Add 500 µl of a secondary blocking buffer (10 mM Tris-Cl (pH 8), 1% BSA, 0.1% T-20, 0.05% $NaN_3$, 0.1 M NaCl), followed by slow shaking at room temperature for 2 h (at 30 rpm on a rotary shaker (Rotation machine)).
12) Wash with 500 µl of a secondary blocking buffer (10 mM Tris-Cl (pH 8), 1% BSA, 0.1% T-20, 0.05% $NaN_3$, 0.1 M NaCl) twice and store in the secondary blocking buffer (the resulting magnetic micro rods are called "RSMPs").

In conclusion, desired antibodies can be coupled to the glass coating of the magnetic micro rods through non-specific reactions. The giant magnetic microrod complexes recognize matrix multiple codes and are bound to antibodies with the highest possible titer. The primary antibodies are antibodies that specifically bind to antigens (TBI biomarkers) corresponding to targets in a sample solution.

Different primary antibodies may be bound to the magnetic micro rods depending on the length of the magnetic micro rods, which form a length coding system that can be used for multiplexed detection assay.

Step 3: QC of Giant Micro Rods Immobilized with Primary Antibodies

1) Place ~30 RSMPs prepared in step 2 in a new 1.5 ml E-tube and remove the supernatant.
2) Add 500 µl of a wash buffer (0.1% BSA, 1×PBS, 0.1% T-20, 0.05% $NaN_3$) and completely remove the 1% BSA/PBS buffer (repeat 2 times).
3) Prepare biotin (2 µg/ml)-conjugated secondary antibodies using a sample buffer (0.1% BSA, 1×PBS, 0.1% T-20).
4) Add 500 µl of the secondary antibody solution prepared in step 3 to the tube from which the wash buffer (0.1% BSA, 1×PBS, 0.1% T-20, 0.05% $NaN_3$) has been removed, followed by slow shaking at room temperature for 1 h (at 30 rpm on a rotary shaker (Rotation machine)).
5) Wash with 500 µl of a wash buffer (0.1% BSA, 1×PBS, 0.1% T-20, 0.05% $NaN_3$) twice (while tapping 30 times).
6) Prepare streptavidin-phycoerythrin (SAPE) whose concentration was adjusted to 2 µg/ml with a sample buffer (0.1% BSA, 1×PBS. 0.1% T-20), add 500 µl of the prepared streptavidin-phycoerythrin, followed by slow shaking for 30 min (at 30 rpm on a rotary shaker (Rotation machine)).
7) Wash with 500 µl of a wash buffer (0.1% BSA, 1×PBS, 0.1% T-20, 0.05% $NaN_3$) twice and measure fluorescence using a fluorescence microscope (Exposure time: 200 ms/gain 5.1×).

Step 4: Preparation of Immunoreactive Materials

A sample solution, giant magnetic microrod complexes immobilized with antibodies specifically binding to antigens corresponding to targets, and secondary antibody-fluorescence material conjugates specifically binding to the antigens were prepared.

The sample solution was a tissue extract, cell lysate, whole blood, plasma, serum, saliva, ocular humor, cerebrospinal fluid, sweat, urine, milk, ascites fluid, synovial fluid or peritoneal fluid.

When it intended to detect a plurality of marker antigens in the sample solution, magnetic micro rods having different shapes (e.g., different lengths) were prepared. Each of the magnetic micro rods was immobilized with an antibody capable of specific binding to and capturing only a specific one of the markers present in the sample solution.

Secondary antibody-fluorescence material conjugates specifically binding to the marker antigens in the sample solution were prepared. An enzyme could be used instead of the fluorescent material.

Step 5: SAMPLE Loading

About 30 giant magnetic microrod complexes (RSMPs) immobilized with antibodies specifically binding to antigens corresponding to markers were introduced into a first well (see FIG. 10).

The RSMPs were transferred to a second well using a magnetic bar. Antigens were diluted 1:1 with a sample diluent (lx PBS, 1% BSA (fatty acid free), 10 mM EDTA (pH 8), 1% T-20, 0.2 mg/mL Tru-Block, 1% human pooling serum) and placed in the second well. 1 µg/ml of the secondary antibodies and 4 µg/ml of SAPE were introduced into the second well (total reaction volume 250 µl).

At this time, since the antigens corresponding to markers were present on the RSMPs in the sample solution (target), first and second immune reactions were induced between the antigens and the RSMPs. The simultaneous first and second immune reactions in the same reactor could shorten the reaction time. It was preferable to use a commonly used well plate having wells arranged at predetermined intervals. A tubular reactor could be used instead of the well plate.

Step 6: Mixing/Heating

The well where step 5 was carried out were placed on a heating block and heated to an appropriately controlled temperature. General immune reactions took place actively at about 35° C. The immunoreactive materials were mixed rapidly while the magnetic bar located above the well continuously moved up and down. This rapid mixing shortened the immune reaction time.

Step 7: Washing

After completion of the reactions, the RSMPs in the second well were washed while sequentially moving them to the third well to the fifth well using the magnetic bar. 250 μl of a wash buffer (0.1% BSA, 1×PBS, 0.1% T-20, 0.05% $NaN_3$) was filled in each of the third to fifth wells and fluorescent materials non-specifically attached to the RSMPs in each well were removed using the magnetic bar for 2 min. Here, the immunoreactive materials were rapidly mixed for washing while the magnetic bar located above the well continuously moved up and down, in the same manner as in step 6.

This washing removed non-specific materials, allowed for washing/recovery of the giant magnetic microrod complexes, and enabled testing of whole blood samples as well as serum and plasma samples.

Step 8: Detection Signal Measurement

After completion of the reactions, detection signals were measured using an ultra-sensitive fluorescent image analyzer specially designed for magnetic particles (see FIG. 11). Code recognition was performed based on image analysis. Multi-detection was achieved even with one fluorescent material. Antigens as single markers as well as fluorescent signals could be detected through enzymatic reactions by ELISA. It took approximately 30 min to complete all the above steps and the limit of detection was approximately several pg/ml to 10,000 pg/ml. As shown in (c) and (d) of FIG. 11, stronger fluorescence was observed when the biomarkers were used at the same concentration.

The ELISA technique was carried out by binding the target materials in the sample to the capture antibodies immobilized onto the giant magnetic microrod complexes and treating the detection antibodies. The detection antibodies were bound to the opposite sides to the sides of the marker materials to which the capture antibodies were bound. An enzyme called horseradish peroxidase (HRP) was conjugated to the detection antibodies. The enzyme used hydrogen peroxide to degrade TMB substrate, giving a color. The chromaticity of the color was determined by the OD value. That is, the method is based on the principle that quantitatively large numbers of the capture antibodies and the detection antibodies are attached in proportion to the amounts of the target materials in the sample, and as a result, the amount of HRP conjugated to the detection antibodies increases, so that the enzymatic reactions proceed relatively rapidly, causing a rapid change in the color of TMB substrate. The amounts of the marker materials in the sample could be determined by previously treating with various concentrations of the marker materials to obtain OD values, drawing a standard curve from the OD values, treating with the actual sample to obtain OD values, and comparing the actual OD values with the standard curve. The concentrations were calculated using a trend line drawn using the data. Here, all OD values and concentrations could be calculated with the automatic analysis program of the analyzer.

The fluorescence measurement technique is based on the same principle as the ELISA technique in that the capture antibodies and the detection antibodies are used for sandwich assay, except that biotin was conjugated to the detection antibodies instead of HRP enzyme and was treated with a streptavidin-conjugated fluorescent material to measure fluorescence values. First, TBI biomarker protein reacted with and was attached to the capture antibodies, followed by treatment with the detection antibodies conjugated with biotin to attach the detection antibodies to the opposite sides to the sides of the TBI biomarker protein to which the capture antibodies were attached. Thereafter, after treatment with e-flour as the fluorescent material conjugated with streptavidin, fluorescent values from the magnetic beads were measured automatically. Based on the principle that higher concentrations of the target diagnostic markers lead to stronger fluorescence signals from the magnetic particles, the locations of the microparticles in the reaction well were identified with a bright field microscope, and fluorescence signals from the corresponding locations were measured in pixels and averaged. The average for ~10 magnetic particles was calculated to determine an average of the fluorescence values.

Fluorescence values were measured in the same manner after reaction with various concentrations of the target marker materials, a standard curve was drawn from the measured fluorescence values, and fluorescence values from the test detection were applied to the standard curve to calculate the concentrations of the corresponding marker proteins in the final sample. The concentrations were calculated using a trend line drawn using the data. Here, all images were analyzed and all fluorescence values were calculated with the automatic analysis program of the analyzer.

The use of the inventive magnetic micro rods for testing the following types of antigens enabled quick testing and multiplexed detection with high accuracy due to quick reactions of the magnetic micro rods.

<Experimental Example 1> GFAP Testing

Capture antibody (GFAP_cAb_09) coupled to the RSMPs prepared by the above method and biotinylated detection Ab (GFAP_dAb_03) were used for GFAP testing. Antigen GFAP (Hytest) was added at concentrations of 0, 20, 50, 100, and 500 pg/ml to serum and applied in the same manner as above.

Tests were conducted using the inventive diagnostic system at GFAP concentrations of 0-500 pg/mL. As a result, the inventive diagnostic system had the same dynamic range (≥log 3) as that of an existing TBI diagnostic test method and showed increased fluorescence signals with increasing GFAP concentration in the range of 0-500 pg/mL, achieving very high correlation values (coefficient of determination, $R^2$: 0.9895) (see FIGS. 13 and 14).

When a black well plate was used in the test using the inventive diagnostic system at an ultra-low GFAP concentration of ≤1 pg/mL, a limit of detection of 0.625 pg/ml was achieved, which was lower than that (20 pg/ml) of an existing test method and corresponded to a ~40-fold increase in sensitivity, suggesting the possibility that the inventive diagnostic system may have at least 100-fold higher sensitivity when optimized (FIG. 17).

Changes in fluorescence intensity with varying silanization times in step 1 were observed. To this end, the same experiment was performed at silanization times of 1 h, 3 h, 9 h, and 24 h. As a result, high fluorescence values were observed from when the silanization time exceeded 9 h and a very insignificant increase was observed after 24 h (see FIG. 7).

<Experimental Example 2> UCH-L1 Testing

Capture antibody (UCH-L1_cAb_02) coupled to the RSMPs prepared by the above method and biotinylated detection Ab (UCH-L1_dAb_07) were used for UCH-L1 testing. Antigen UCH-L1_Ag-08 (EzDiatech) was added at concentrations of 0, 100, 300, 500, and 1000 pg/ml to serum and was allowed to react with the antibodies in the same manner as above.

Tests were conducted using the inventive diagnostic system at UCH-L1 concentrations of 0-500 pg/mL. As a result, the inventive diagnostic system had the same dynamic range (≥log 3) as that of an existing TBI diagnostic test method and showed increased fluorescence signals with increasing UCH-L1 concentration in the range of 0-500 pg/mL, achieving very high correlation values (coefficient of determination, $R^2$: 0.9894) (see FIGS. 15 and 16).

<Experimental Example 3> Multiplexed Detection of GFAP and UCH-L1

A multiplex assay for GFAP (on 300 μm magnetic particles) and UCH-L1 (on 400 μm magnetic particles) was conducted using the inventive diagnostic system. The results are shown in FIG. 12. Fluorescence signals from only the magnetic particles bound with the specific antigen added for immune reactions were detected depending on the concentration of the antigen. That is, desired magnetic micro rods could be identified and detected by their lengths on particle images (bright field) and fluorescence signals of desired biomarkers bound to the magnetic micro rods could be detected and analyzed on fluorescent images (FIG. 18).

<Experimental Example 4> Interferon Gamma (IFN-γ) Testing

Tests were conducted using the inventive diagnostic system at interferon gamma (IFN-γ) concentrations of 0-1000 pg/mL. As a result, the inventive diagnostic system had a dynamic range (3-5logs) comparable to that of an existing TBI diagnostic test method and showed increased fluorescence signals with increasing IFN-γ concentration in the range of 0-1000 pg/mL, achieving very high correlation values (see FIGS. 19 and 20).

When a black well plate was used in the test using the inventive diagnostic system at an ultra-low IFN-γ concentration of ≤1 pg/mL, a limit of detection of 0.625 pg/ml was achieved, which was lower than that (20 pg/ml) of an existing test method and corresponded to a ~40-fold increase in sensitivity, suggesting the possibility that the inventive diagnostic system may have at least 100-fold higher sensitivity when optimized (FIG. 21).

<Experimental Example 5> Multiplexed Detection of IL-10 and Interferon Gamma (IFN-γ)

A multiplex assay for IL-10 (on 400 μm magnetic particles) and IFN-γ (on 300 μm magnetic particles) was conducted using the inventive diagnostic system. As a result, desired magnetic micro rods could be identified and detected by their lengths on particle images (bright field) and fluorescence signals of desired biomarkers bound to the magnetic micro rods could be detected and analyzed on fluorescent images in the same manner as in Experimental Example 3.

Although the particulars of the present invention have been described in detail, it will be obvious to those skilled in the art that such particulars are merely preferred embodiments and are not intended to limit the scope of the present invention. Therefore, the true scope of the present invention is defined by the appended claims and their equivalents.

The invention claimed is:

1. Magnetic particles comprising:

a core comprising a magnetically responsive metal, a shell layer surrounding the core and having a uniform thickness of 4 to 8 μm, and capture probes immobilized on a surface of the shell layer to capture biological materials, wherein, the shell layer is treated with an acidic solution comprising a mixture of a strong acid and hydrogen peroxide in a volume ratio of 1:1 to 7:1, the shell layer has an average surface roughness (Ra) of 1 to 15 nm, the surface of the shell layer has hydrophilic functional groups at a density of 1 to 80 groups per $nm^2$; and the capture probes are linked to the hydrophilic functional groups on the surface of the shell layer, wherein each of the capture probes comprises an antibody against a biomarker for the diagnosis of a traumatic brain injury or infectious disease as an antigen.

2. The magnetic particles according to claim 1, wherein the magnetic particles have a limit of detection of greater than 0 and not more than 1 pg/ml and a dynamic range of at least log 3.

3. The magnetic particles according to claim 1, wherein the magnetic particles have two or more different lengths and diagnose two or more types of biomarkers simultaneously.

4. The magnetic particles according to claim 1, wherein the hydrophilic functional groups are silanol groups or carboxyl, amino, hydroxyl, thiol, or aldehyde groups derived from silanol groups.

5. The magnetic particles according to claim 1, wherein the core occupies 60% to 99% of the total volume of the magnetic particles.

6. The magnetic particles according to claim 1, wherein the shell layer has an average surface roughness (Ra) of 1 to 10 nm.

7. The magnetic particles according to claim 1, wherein the magnetic particles are obtained by cutting glass-coated metal microwires.

8. The magnetic particles according to claim 1, wherein the magnetic particles have a length of 50 to 500 μm and a specific gravity of 5 to 30, such that they are not suspended in water.

9. The magnetic particles according to claim 1, wherein the magnetic particles are in the form of micro rods.

10. The magnetic particles according to claim 9, wherein the micro rods have a length of 10 to 1,000 μm.

11. The magnetic particles according to claim 9, wherein the micro rods have an aspect ratio of at least 2.

12. The magnetic particles according to claim 1, wherein the biomarker is-recited in claim 1 is present in a sample solution derived from a living organism.

13. A method for preparing magnetic particles comprising:

(i) preparing magnetic micro rods comprising a core comprising a magnetic material and a shell layer made of glass and having a uniform thickness of 4 to 8 μm;

(ii) treating a surface of the magnetic micro rods with an acidic solution comprising a mixture of a strong acid and hydrogen peroxide in a volume ratio of 1:1 to 7:1 to form silanol groups on the surface of the shell layer;

(iii) immersing the surface-treated magnetic microrods micro rods-in a silane-based solution to bind silane molecules to the silanol groups;

(iv) converting terminal groups of the silane molecules to functional groups capable of binding to probes; and (v) attaching probes to the functional groups, wherein, the shell layer obtained by the acidic treatment has an average surface roughness (Ra) of 1 to 15 nm, and the surface of the shell layer has hydrophilic functional groups at a density of 1 to 80 groups per $nm^2$.

14. The method according to claim 13, wherein step (iii) is carried out by immersing the surface-treated magnetic microrods in the silane-based solution for 6 to 24 hours.

15. The method according to claim 13, wherein the acidic solution is a mixture of sulfuric acid and hydrogen peroxide.

* * * * *